(12) United States Patent
Lopez Vales et al.

(10) Patent No.: US 11,583,511 B2
(45) Date of Patent: Feb. 21, 2023

(54) MARESINS FOR USE IN THE TREATMENT OF CNS INJURIES

(71) Applicants: UNIVERSITAT AUTONOMA DE BARCELONA, Bellaterra Barcelona (ES); OHIO STATE UNIVERSITY, Columbus, OH (US); THE ROYAL INSTITUTION FOR THE ADVANCEMENT OF LEARNING/MCGILL UNIVERSITY, Montreal (CA)

(72) Inventors: Ruben Lopez Vales, Bellaterra (ES); Isaac Francos Quijorna, Bellaterra (ES); Jan Markus Schwab, Columbus, OH (US); Samuel David, Montreal (CA)

(73) Assignees: UNIVERSITAT AUTONOMA DE BARCELONA, Bellaterra Barcelona (ES); OHIO STATE UNIVERSITY, Columbus, OH (US); THE ROYAL INSTITUTION FOR THE ADVANCEMENT OF LEARNING/MCGILL UNIVERSITY, Montreal (CA)

(*) Notice: Subject to any disclaimer, the term of this patent is extended or adjusted under 35 U.S.C. 154(b) by 109 days.

(21) Appl. No.: 16/631,615

(22) PCT Filed: Jul. 20, 2017

(86) PCT No.: PCT/IB2017/054398
§ 371 (c)(1),
(2) Date: Jan. 16, 2020

(87) PCT Pub. No.: WO2019/016580
PCT Pub. Date: Jan. 24, 2019

(65) Prior Publication Data
US 2020/0163923 A1   May 28, 2020

(51) Int. Cl.
| | |
|---|---|
| *A61K 31/202* | (2006.01) |
| *A61K 8/36* | (2006.01) |
| *A61K 9/00* | (2006.01) |
| *A61P 25/28* | (2006.01) |
| *A23L 33/12* | (2016.01) |
| *A23L 33/00* | (2016.01) |

(52) U.S. Cl.
CPC ............ *A61K 31/202* (2013.01); *A23L 33/12* (2016.08); *A61K 8/361* (2013.01); *A61K 9/0019* (2013.01); *A61K 9/0053* (2013.01); *A61P 25/28* (2018.01); *A23L 33/30* (2016.08)

(58) Field of Classification Search
CPC .. A61K 31/201; A61K 31/202; A61K 31/231; A61K 31/232; A61K 8/361; A61K 9/0019; A61K 9/0053; A23L 33/12; A23L 33/30; A61P 25/28; A61P 25/18
See application file for complete search history.

(56) References Cited

U.S. PATENT DOCUMENTS

| | | |
|---|---|---|
| 5,441,951 A | 8/1995 | Serhan |
| 8,927,747 B2 | 1/2015 | Serhan et al. |
| 9,340,483 B2 | 5/2016 | Gjorstrup |
| 9,416,118 B2 | 8/2016 | Serhan et al. |
| 9,463,177 B2 | 10/2016 | Conte et al. |
| 10,154,977 B2 | 12/2018 | Serhan et al. |
| 10,653,703 B2 | 5/2020 | Serhan et al. |
| 2005/0075398 A1 | 4/2005 | Bazan et al. |
| 2013/0302343 A1 | 11/2013 | Becher et al. |
| 2015/0018417 A1 | 1/2015 | Freeman et al. |
| 2015/0126602 A1 | 5/2015 | Bannenberg et al. |
| 2016/0367510 A1 | 12/2016 | Mathisen |
| 2020/0038356 A1 | 2/2020 | Lopez Vales et al. |

FOREIGN PATENT DOCUMENTS

| | | | | |
|---|---|---|---|---|
| CN | 102021075 A | | 4/2011 | |
| WO | WO-2012135032 A2 | * | 10/2012 | ........... A61K 31/202 |
| WO | WO-2017041094 A1 | * | 3/2017 | ............... A23D 9/00 |
| WO | 2019/016580 A1 | | 1/2019 | |

OTHER PUBLICATIONS

Francos-Quijorna et al., "Maresin-1 promotes inflammatory resolution, neuroprotection and functional neurological recovery after spinal cord injury", Glia, vol. 65(suppl. 1), p. E458, publ. Jun. 2017 (Year: 2017).*
Crane et al., JAMA Neurol., vol. 73(9), pp. 1062-1069, publ. Jul. 11, 2016 (Year: 2016).*
International Search Report and Written Opinion for PCT/IB2017/054398, dated Nov. 17, 2017, 10 pages.
Akagi et al., Systemic delivery of proresolving lipid mediators resolvin D2 and maresin 1 attenuates intimal hyperplasia in mice, The FASEB Journal 2015, vol. 29, pp. 2504-2513.
Arnold et al., Inflammatory monocytes recruited after skeletal muscle injury switch into antiinflammatory macrophages to support myogenesis, The Journal of Experimental Medicine, 2007, vol. 204 (5), pp. 1057-1069.
Batchelor et al., Comparison of Inflammation in the Brain and Spinal Cord following Mechanical Injury, Journal of Neurotrauma, 2008, vol. 25, pp. 1217-1225.
Buckley et al., Pro-Resolving lipid mediators and Mechanisms in the resolution of acute inflammation, Immunity, 2014, vol. 40(3), pp. 1-26.
Coll-Miro et al., Beneficial effects of IL-37 after spinal cord injury in mice, PNAS, 2016, vol. 113 (5), pp. 1411-1416.
David et al., Harmful and Beneficial Effects of Inflammation after Spinal Cord Injury: Potential Therapeutic Implications, Handbook of Clinical Neurology, vol. 109 (3), pp. 1-59.
David et al., Role of phospholipase A2s and lipid mediators in secondary damage after spinal cord injury, Cell Tissue Res, 2012, vol. 349, pp. 249-267.

(Continued)

*Primary Examiner* — Sarah Pihonak
(74) *Attorney, Agent, or Firm* — Sterne, Kessler, Goldstein & Fox P.L.L.C.

(57) ABSTRACT

The present invention relates to maresins, preferably maresin-1, for use in the treatment of CNS injuries preferably selected from spinal cord injury and traumatic brain injury.

17 Claims, 8 Drawing Sheets

(56) References Cited

OTHER PUBLICATIONS

David et al., Repertoire of microglial and macrophage responses after spinal cord injury, Nature Reviews Neuroscience, 2011, vol. 12, pp. 388-399.

Fawcet et al., Defeating inhibition of regeneration by scar and myelin components, Handbook of Clinical Neurology, 2012, vol. 109 (3), pp. 503-522.

Francos-Quijorna et al., IL-4 Drives Microglia and Macrophages Toward a Phenotype Conducive for Tissue Repair and Functional Recovery After Spinal Cord Injury, GLIA, 2016, vol. 64 (12), pp. 2079-2092.

Issac Francos Quijoma, Activation of inflammatory resolution programs as a new therapeutic approach to promote neuroprotection after SCI, Jul. 22, 2016, Universitat Autonoma de Barcelona, pp. 1-257.

Gomez-Nicola et al., Microglial Dynamics and Role in the Healthy and Diseased Brain: A Paradigm of Funcional Plasticity, The Neuroscientist, 2015, vol. 21 (2), pp. 169-184.

Harrison et al., Resolvins AT-D1 and E1 differentially impact functional outcome, post-traumatic sleep, and microglial activation following diffuse brain injury in the mouse, Brain Behavior, and Immunity, 2015, vol. 47, pp. 1-23.

Hawthorne et al., Emerging Concepts in Myeloid Cell Biology after Spinal Cord Injury, Neurotherapeutics: The Journal of the American Society for Experimental NeuroTherapeutics, 2011, vol. 8, pp. 252-261.

Kroner et al., TNF and Increased Intracellular Iron Alter Macrophage Polarization to a Detrimental M1 Phenotype in the Injured Spinal Cord, Neuron, 2014, vol. 83, pp. 1098-1116.

Lu et al., Signaling regulations of neuronal regenerative ability, Current Opinion in Neurobiology, 2014, vol. 27, pp. 135-142.

Marcheselli et al., Novel Docosanoids Inhibit Brain Ischemia-Reperfusion-mediated Leukocyte Infiltration and Pro-Inflammatory Gene Expression, The Journal of Biological Chemistry, 2003, vol. 278 (44), pp. 43807-43817.

Michael-Titus et al., Omega-3 fatty acids and traumatic neurological injury: from neuroprotection to neuroplasticity?, Trends in Neurosciences, 2014, vol. 37 (1), pp. 30-38.

Nahrendort, The healing myocardium sequentially mobilizes two monocyte subsets with divergent and complementary functions, The Journal of Experimental Medicine, 2007, vol. 204 (12), pp. 3037-3047.

Popovich et al., Can the immune system be harnessed to repair the CNS?, Nature Reviews Neuroscience, 2008, vol. 9, pp. 481-493.

Santos-Nogueira et al., Activation of Lysophosphatidic Acid Receptor Type 1 Contributes to Pathophysiology of Spinal Cord Injury, The Journal of Neuroscience, 2015, vol. 35 (28), pp. 10224-10235.

Schwab et al., Resolvin E1 and Protectin D1 Activate Inflammation-Resolution Programs, Nature, 2007, vol. 447 (7146), pp. 1-15.

Charles N. Serhan, Novel Pro-Resolving Lipid Mediators in Inflammation Are Leads for Resolution Physiology, Nature, 2014, vol. 510 (7503), pp. 1-24.

Serhan et al., Protectins and Maresins: New Pro-Resolving Families of Mediators in Acute Inflammation and Resolution Bioactive Metabolome, Biochim Biophys Acta., 2015, vol. 1851 (4), pp. 1-40.

Serhan et al., Maresins: novel macrophage mediators with potent antiinflammatory and proresolving actions, The Journal of Experimental Medicine, 2009, vol. 206 (1), pp. 15-23.

Lawrence Steinman, No. quiet surrender: molecular guardians in multiple sclerosis brain, The Journal of Clinical Investigation, 2015, vol. 125 (4), pp. 1371-1378.

Stenudd et al., Role of Endogenous Neural Stem Cells in Spinal Cord Injury and Repair, JAMA Neurology, 2015 vol. 72 (2), pp. 235-237.

Svensson et al., Lipoxins and aspirin-triggered lipoxin inhibit inflammatory pain processing, The Journal of Experimental Medicine, 2007, vol. 204 (2), pp. 245-252.

Xian et al., The pro-resolving lipid mediator Maresin 1 protects against cerebral ischemia/reperfusion injury by attenuating the pro-inflammatory response, Biochemical and Biophysical Research Communications, 2016, pp. 175-181.

Abdulnour et al., Maresin 1 biosynthesis during platelet-neutrophil interactions is organ-protective, PNAS, 2014, vol. 111 (46), pp. 16526-16531.

Basso et al., Basso Mouse Scale for Locomotion Detects Differences in Recovery after Spinal Cord Injury in Five Common Mouse Strains, Journal of Neurotrauma, 2006, vol. 23 (5), pp. 635-659.

Dalli et al., The novel 13S,14S-epoxy-maresin is converted by human macrophages to maresin 1 (MaR1), inhibits leukotriene A4 hydrolase (LTA4H), and shifts macrophage phenotype, The FASEB Journal, 2013, vol. 27, pp. 2573-2583.

David et al., Macrophage and Microglial Plasticity in the Injured Spinal Cord, Neuroscience Forefront Review, Neuroscience 307, 2015, pp. 311-318.

Deng et al., Maresin Biosynthesis and Identification of Maresin 2, a New Anti-Inflammatory and Pro-Resolving Mediator from Human Macrophages, Plos One, 2014, vol. 9 (7), pp. 1-9.

Hassan et al., Acute Changes in Dietary w-3 and w-6 Polyunsaturated Fatly Acids Have a Pronounced Impact on Survival following Ischemic Renal Injury and Formation of Renoprotective Docosahexaenoic Acid-Derived Protectin D1, The Journal of Immunology, 2009, vol. 182 , pp. 3223-3232.

Huang et al., A combination of intravenous and dietary docosahexaenoic acid significantly improves outcome after spinal cord injury, Brain, 2007, pp. 3004-3019.

King et al., Omega-3 Fatty Acids Improve Recovery, whereas Omega-6 Fatty Acids Worsen Outcome, after Spinal Cord Injury in the Adult Rat, The Journal of Neuroscience, 2006, vol. 26 (17), pp. 4672-4680.

Lopez-Vales et al., Fenretinide Promotes Functional Recovery and Tissue Protection after Spinal Cord Contusion Injury in Mice, The Journal of Neuroscience, 2010, vol. 30 (9), pp. 3220-3226.

Macron et al., Maresin 1, a Proresolving Lipid Mediator Derived from Omega-3 Polyunsaturated Fatty Acids, Exerts Protective Actions in Murine Models of Colitis, The Journal of Immunology, 2013, vol. 191, pp. 4288-4298.

Murray et al., Macrophage activation and polarization: nomenclature and experimental guidelines, Immunity, 2014, vol. 41 (1), pp. 1-14.

Phillip G. Popovich, Neuroimmunology of traumatic spinal cord injury: A brief history and overview, Experimental Neurology 258, 2014, pp. 1-4.

Pruss et al., Non-Resolving Aspects of Acute Inflammation after Spinal Cord Injury (SCI): Indices and Resolution Plateau, Brain Pathology, 2011, vol. 21, pp. 652-660.

Serhan et al., Macrophage proresolving mediator maresin 1 stimulates tissue regeneration and controls pain, The FASEB Journal, 2012, vol. 26, pp. 1755-1765.

Zhu et al., Pro-resolving lipid mediators improve neuronal survival and increase AB42 phagocytosis, Mol Neurobiol., 2016, vol. 53 (4), pp. 1-32.

Bazan N.G, "Neuroprotectin D1-mediated anti-inflammatory and survival signaling in stroke, retinal degenerations, and Alzheimer's disease," *Journal of Lipid Research* 50: S400-S405, Americal Society for Biochemistry and Molecular Biology, United States (2009).

Bazan N.G et al., "Novel aspirin-triggered neuroprotectin D1 attenuates cerebral ischemic injury after experimental stroke," *Experimental Neurology* 236(1):122-130, Elsevier, Netherlands (2012).

Crane P.K. et al., "Association of Traumatic Brain Injury with Late-Life Neurodegenerative Conditions and Neuropathologic Findings," *JAMA Neurol* 73(9)A062-1069, American Medical Association, United States (2016).

Cudkowicz M.E. et al., "Trial of Celecoxib in Amyotrophic Lateral Sclerosis," *Ann. Neurol.* 60(1):22-31, Wiley Periodicals, United States (2006).

Francos-Quijorna I. et al., "Maresin-1 Promotes Inflammatory Resolution, Neuroprotection and Functional Neurological Recovery After Spinal Cord Injury," *The Journal of Neuroscience* 37(48):11731-11743, Society for Neuroscience, United States (2017).

Guanghao L. et al., "Neuronal phagocytosis by inflammatory macrophages in ALS spinal cord: inhibition of inflammation by

(56) References Cited

OTHER PUBLICATIONS resolving D1," *American Journal of Neurodegenerative Disease*, 1(1):60-74, e-Century Publishing, United States (2012).

Schawanke R.C. et al., "EPA- and DHA-derived resolvins' actions in inflammatory bowel disease," *European Journal of Pharmacology* 785:156-164, Elsevier, Netherlands (2015).

Tian Y. et al., "Resolvin D2 recovers neural injury by suppressing inflammatory mediators expression in lipopolysaccharide-induced Parkinson's disease rat model," *Biochemical and Biophysical Research Communications* 460(3):799-805, Elsevier, Netherlands (2015).

"TNF neutralization in MS: Results of a randomized, placebo-controlled multicenter study," The Lenercept Multiple Sclerosis Study Group and The University of British Columbia MS/MRI Analysis Group, *Neurology* 53(3):457-465, American Academy of Neurology, United States (1999).

\* cited by examiner

A

B

C

A Saline

B MaR1

MARESINS FOR USE IN THE TREATMENT OF CNS INJURIES

CROSS-REFERENCE TO RELATED APPLICATIONS

This application is a National Phase of International Application No. PCT/IB2017/054398, filed Jul. 20, 2017, which designated the U.S. and that International Application was published under PCT Article 21(2) in English.

FIELD OF THE INVENTION

The present invention relates to the field of methods of treating CNS injuries, in particular spinal cord injury and/or traumatic brain injury. More particularly, the present invention relates to maresins, preferably maresin-1, and compositions comprising thereof, for use in the treatment of CNS injuries, in particular spinal cord injury and/or traumatic brain injury.

BACKGROUND OF THE INVENTION

Spinal cord injury (SCI) is defined as any injury, wound, or damage to the spinal cord that results in a loss of function, such as mobility or feeling. Frequent causes of damage are trauma (e.g., by car accident, gunshot, falls, etc.) or disease (polio, spina bifida, Friedreich's Ataxia, etc.). The spinal cord does not have to be severed in order for a loss of functioning to occur. In most individuals with SCI, the spinal cord is intact, but the damage results in loss of function. Besides a loss of sensation or motor function, individuals with SCI may also experience symptoms, conditions, or impairments including dysfunction of the bowel and bladder, sexual and fertility dysfunction, inability to regulate blood pressure effectively, reduced control of body temperature, inability to sweat below the level of injury, and chronic pain. A patient with SCI can have any level of SCI, as typically defined by the level of the damage (e.g., at or below any of the eight cervical vertebrae or the twelve thoracic vertebrae). Very high injuries (C-1, C-2) can result in a loss of many involuntary functions including the ability to breathe, necessitating breathing aids such as mechanical ventilators or diaphragmatic pacemakers.

Traumatic brain injury (TBI) is defined as any injury, wound, or damage caused by any type of trauma to the head, such as impact to the head or shaking. More specifically, TBI is an acquired injury to the brain caused by an external physical force, resulting in total or partial functional disability or psychosocial impairment, or both. The term applies to open and closed head injuries resulting in impairments in one or more areas, such as cognition; language; memory; attention; reasoning; abstract thinking; judgment; problem-solving; sensory, perceptual, and motor abilities; psychosocial behavior; physical functions; information processing; and speech. The term typically does not apply to brain injuries that are congenital or degenerative, or brain injuries induced by birth trauma, although the latter type of trauma may also be treated using the method of the invention. TBI can result in a variety of physiological and psychological symptoms, conditions or impairments, including physical impairments (e.g., speech, vision, hearing and other sensory impairment; headaches; lack of fine motor coordination; spasticity of muscles; paresis or paralysis of one or both sides and seizure disorders; balance impairments; and other gait impairments), cognitive impairments (e.g., short- and long-term memory deficits, impaired concentration, slowness of thinking and limited attention span, as well as impairments of perception, communication, reading and writing skills, planning, sequencing, and judgment), and psychosocial-behavioral-emotional impairments (e.g., fatigue, mood swings, denial, self-centeredness, anxiety, depression, lowered self-esteem, sexual dysfunction, restlessness, lack of motivation, inability to self-monitor, difficulty with emotional control, inability to cope, agitation, excessive laughing or crying, and difficulty relating to others).

In particular, spinal cord injury (SCI) causes an immune response (David et al., 2012a; Gomez-Nicola and Perry, 2015; Steinman, 2015) composed of activated resident glial cells (microglia and astrocytes) and blood-derived leukocytes (neutrophils, monocytes and lymphocytes) that enter the damaged spinal cord (Hawthorne and Popovich, 2011; Pruss et al., 2011; David et al., 2012a). These immune cells are required for effective clearance of damaged cell and myelin debris, and for the release of bioactive molecules that lead to tissue healing and repair (Popovich and Longbrake, 2008; David et al., 2012a). However, they also secrete several factors that mediate cytotoxicity to neurons, glia, axons and myelin (Popovich and Longbrake, 2008; David et al., 2012a). Hence, the inflammatory response exerts both, helpful and detrimental actions after SCI, and thus, its final outcome on this pathology will depend on the balance between mechanisms that regulate different aspects of the inflammatory response.

A self-limited inflammatory response is a prerequisite for a return to homeostasis (catabasis) and requires effective resolution of inflammation (Buckley et al., 2014; Serhan, 2014; Serhan et al., 2015). By contrast, insufficient or inadequate resolution leads to chronic inflammation that causes greater tissue damage, impaired tissue remodeling and inappropriate tissue healing, such as pronounced deposition of extracellular matrix (Buckley et al., 2014; Serhan, 2014; Serhan et al., 2015). This is also the case after SCI, where inflammation fails to resolve properly leading to disproportionate harmful bystander side effects (Hawthorne and Popovich, 2011; Pruss et al., 2011; David et al., 2012a). The damaging consequences of non-resolving inflammation are pronounced in the lesioned spinal cord due to the limited capacity of repair, such as axon regeneration and replacement of damaged neurons and myelin, leading to irreversible functional disabilities (Fawcett et al., 2012; Lu et al., 2014; Stenudd et al., 2015).

Resolution of inflammation is an active process regulated, in part, by a superfamily of lipid mediators derived from poly-unsaturated fatty acid (PUFA) (Schwab et al., 2007; David et al., 2012c; Serhan, 2014). This super-family of specialized pro-resolving mediators (SPM) include: lipoxins, resolvins (RvD and RvE), protectins and maresins (Buckley et al., 2014; Serhan, 2014; Serhan et al., 2015). SPM actively turn off the inflammatory response by acting on distinct G protein coupled receptors expressed on immune cells that activates dual anti-inflammatory and pro-resolution programs (Buckley et al., 2014; Serhan, 2014; Serhan et al., 2015). Among the anti-inflammatory actions of SPMs include the induction in the expression of anti-inflammatory cytokines or inflammatory scavenging molecules such as IL-10, IL-1 decoy receptors and IL-1 receptor antagonists (Buckley et al., 2014; Serhan, 2014). On the other hand, SPM activate specific mechanisms that trigger the resolution of inflammation, which include: (i) down-regulation of pro-inflammatory cytokines; (ii) abrogation of intracellular pathways that lead to inflammation; (iii) clearance of inflammatory cell detritus (such as apoptotic neutrophils) by macrophages and (iv) normalization of immune cells counts to basal levels also referred to as catabasis (Buckley et al., 2014; Serhan, 2014; Serhan et al., 2015). The importance of SPM in the resolution of inflammation is evident in many chronic pathological conditions where their production is insufficient, delayed or even absent; and exogenous administration of SPMs reduce inflammation and mediate tissue protection (Schwab et al., 2007; Buckley et al., 2014). However, it is currently not known whether sustained inflammation in SCI is due to inadequate production of SPMs.

The present inventors have surprisingly found that SPM biosynthesis is impaired after SCI and that systemic administration of MaR1 (Serhan et al., 2009), a DHA-derived SPM, is able to enhance resolution of inflammation, resulting in improved functional and histopathological outcomes. These results provide strong evidence about the beneficial effects of exogenous administration of MaR1 in a pre-clinical model of SCI, and suggest that administration of SPMs could be a novel therapeutic approach to treat acute SCI in humans, for which there is currently no effective treatment. Nevertheless, the present inventors firmly believe that results provided in the present document can also be applicable to general CNS injuries in view of the underlying mechanism of action of the compounds disclosed herein, being a particular example the TBI. See Peter E. Batchelor et al. Comparison of inflammation in the brain and spinal cord following mechanical injury. Journal of Neurotrauma. 25: 1217-1225 (October 2008). Accordingly, the present inventors provides a method of treating CNS injuries, preferably selected from spinal cord injury and traumatic brain injury, by administering these molecules called "Specialized pro-resolving lipid mediator" or "SPM", in particular maresins, preferably maresin-1.

The thesis (Francos-Quijorna, 2016) discloses the invention by one of the inventors.

SUMMARY OF THE INVENTION

Figure 1:
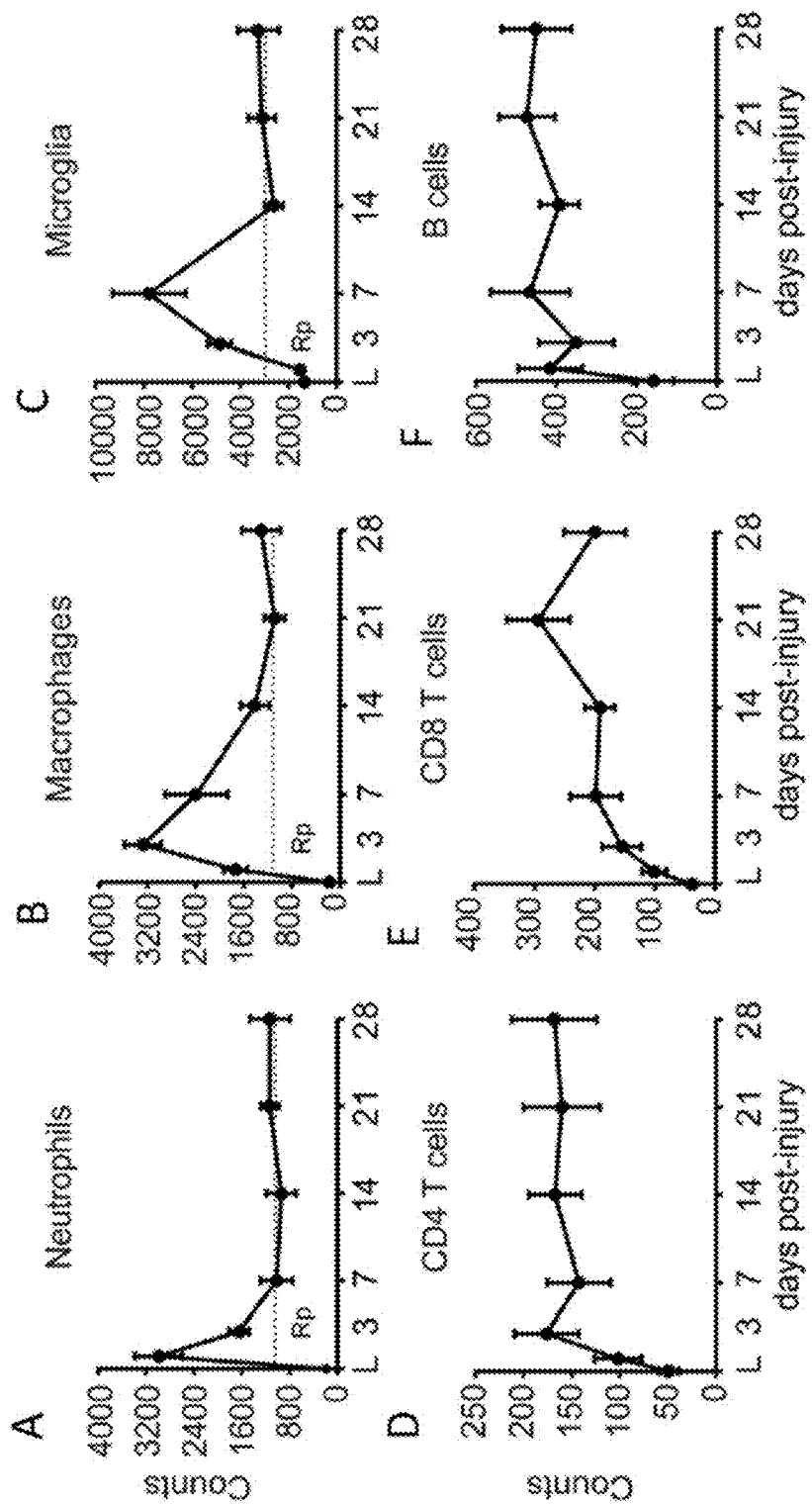
FIG. 1. Temporal dynamics of changes in leukocyte numbers at the lesion-site after SCI in mice. (A-F) Graphs showing neutrophil (A) macrophage (B), microglial (C), CD4 T cell (D), CD8 T cell (E) and B cell (F) kinetics in the contused spinal cord for the first 4 weeks. Note that the counts for the different immune cell populations remained elevated throughout this period. Dash lines indicates the resolution plateau (Rp). * p<0.05 vs Laminectomy (L). One Way ANOVA with Tuckey's post hoc correction (n=8 per point). Error bars indicate SEM.

The present invention relates to maresins, preferably maresin-1, alone or combined with at least one specialized pro-resolving lipid mediator selected from other maresin, resolvin D1, resolving D2, resolving D3, resolvin D4, resolvin E1, resolvin E2, protectin D1, neuroprotection D1, lipoxin A4 and aspirin-triggered lipoxin for use in the treatment of CNS injuries, preferably selected from spinal cord injury and traumatic brain injury.

The present invention further relates to a composition comprising maresins, preferably maresin-1, alone or combined with at least one specialized pro-resolving lipid mediator selected from other maresin, resolvin D1, resolving D2, resolving D3, resolvin D4, resolvin E1, resolvin E2, protectin D1, neuroprotection D1, lipoxin A4 and aspirin-triggered lipoxin, for use in the treatment of CNS injuries, preferably selected from spinal cord injury and traumatic brain injury.

DETAILED DESCRIPTION OF THE INVENTION

The present invention relates to maresins (i.e. maresin-1 or marein-2 or a combination thereof) for use in the treatment of CNS injuries. In a preferred embodiment, said CNS injuries selected from spinal cord injury and traumatic brain injury. In another preferred embodiment, the present invention relates to maresin-1 for use in the treatment of CNS injuries. In a further preferred embodiment, said CNS injuries selected from spinal cord injury and traumatic brain injury.

The term "CNS injuries" is understood in the context of the present invention as including, but not limited thereto, neurological traumas and injuries, surgery related trauma and/or injury, retinal injury and trauma, injury related to epilepsy, cord injury, spinal cord injury, traumatic brain injury, brain injury, brain surgery, trauma related brain injury, trauma related to spinal cord injury, brain injury related to cancer treatment, spinal cord injury related to cancer treatment, brain injury related to infection, brain injury related to inflammation, spinal cord injury related to infection, spinal cord injury related to inflammation, brain injury related to environmental toxin, and spinal cord injury related to environmental toxin.

Said maresins, preferably maresin-1, can be used alone or combined with other specialized pro-resolving lipid mediators when treating said CNS injuries, preferably selected from spinal cord injury and traumatic brain injury.

Maresin-1 (7(R)-MaR1 or simply MaR1) is a 7,14-dihydroxy DHA formed from 14(S)-hydroperoxy DHA supplied exogenously to resident peritoneal mouse macrophages activated with zymosan A.

Maresin-2 (also termed as MaR2) is a 13R,14S-dihydroxy DHA formed by recombinant human macrophage 12-lipoxygenase and soluble epoxide hydrolase co-incubated with DHA.

A "Specialized pro-resolving lipid mediator" (SPM, also termed specialized pro-resolving mediators) is a large and growing class of cell signaling molecules formed in cells by the metabolism of polyunsaturated fatty acids (PUFA) by one or a combination of lipoxygenase, cyclooxygenase, and cytochrome P450 monooxygenase enzymes. Pre-clinical studies, primarily in animal models and human tissues, implicate SPM in orchestrating the resolution of inflammation. These studies suggest that synthetic SPM that are resistant to being metabolically inactivated hold promise of being clinically useful pharmacological tools for preventing and resolving a wide range of pathological inflammatory responses along with the tissue destruction and morbidity that these responses cause. These molecules include maresins (maresin-1 and maresin-2), D-series resolvins (resolvin D1, D2 D3 or D4), E-series resolvins (resolvin E1 or E2, protectins (protectin D1 or neuroprotection D1) and lipoxins (lipoxin A4 or aspirin-triggered lipoxin). Lipoxins are derived from arachidonic acid, E-series resolvins are derived from the long-chain n-3 fatty acid eicosapentaenoic acid (EPA) and D-series resolvins, protectins/neuroprotectins and maresins, are all derived from the n-3 fatty acid docosahexaenoic acid (DHA). There is mounting evidence for the role of these compounds in inflammation processes.

In a preferred embodiment, the maresin, preferably maresin-1, is combined with at least one specialized pro-resolving lipid mediator selected from other maresin, resolvin D1, resolving D2, resolving D3, resolvin D4, resolvin E1, resolvin E2, protectin D1, neuroprotection D1, lipoxin A4 and aspirin-triggered lipoxin, for use in the treatment of CNS injuries. Note that if maresin-2 is used as a main compound, this can also be combined with at least maresin-1.

In another preferred embodiment, the maresin, preferably maresin-1, is combined with at least one specialized proresolving lipid mediator selected from other maresin, resolvin D1, resolving D2, resolving D3, resolvin D4, resolvin E1, resolvin E2, protectin D1, neuroprotection D1, lipoxin A4 and aspirin-triggered lipoxin, for use in the treatment of spinal cord injury. Note that if maresin-2 is used as a main compound, this can also be combined with at least maresin-1.

In a further preferred embodiment, the maresin, preferably maresin-1, is combined with at least one specialized pro-resolving lipid mediator selected from other maresin, resolvin D1, resolving D2, resolving D3, resolvin D4, resolvin E1, resolvin E2, protectin D1, neuroprotection D1, lipoxin A4 and aspirin-triggered lipoxin, for use in the treatment of traumatic brain injury. Note that if maresin-2 is used as a main compound, this can also be combined with at least maresin-1.

Resolvin E1 (RvE1) is 5S,12R,18R-trihydroxy-eicosa-6Z,8E,10E,14Z,16E-pentaenoic acid). Resolvin E2 (RvE2) is 5S, 18-dihydroxy-eicosa-6E,8Z,11Z, 14Z,16E-pentaenoic acid). Protectin D1 (PD1) is 10R,17S-dihydroxy-docosa-4Z, 7Z,11E,13E,15Z,19Z-hexaenoic acid). Resolvin D1 (RvD1) is 7S,8R,17S-trihydroxy-docosa-4Z,9E,11E,13Z,15E,19Z-hexaenoic acid). Resolvin D2 (RvD2) is 7S, 16R, 17S-trihydroxy-docosa-4Z,8E, 10Z,12E,14E,19Z-hexaenoic acid). Resolvin D3 (RvD3) is 4S,11R,17S-trihydroxy-docosa-5Z,7E,9E,13Z,15E,19Z-hexaenoic acid). Resolvin D4 (RvD4) is 4S,5,17S-trihydroxy-docosa-6E,8E,10Z,13Z, 15E,19Z-hexaenoic acid). Lipoxin A4 (LXA4) is 5S,6R, 15S-trihydroxy-eicosa-7E,9E, 11Z, 13E-tetraenoic acid).

In a particular embodiment, maresins, i.e maresin-1 or maresin-2, preferably maresin-1, and/or any of the specialized pro-resolving lipid mediator which can be combined with maresin-1 or maresin-2, can be in the form of a tautomer, solvate, hydrate, or a pharmaceutically acceptable salt thereof, providing that the chemical structure of these compounds allows to be present in these forms.

"Pharmaceutically acceptable salt" as used herein means that the salt derived from the corresponding compound is suitable for administration to a subject to achieve the treatments described herein, without unduly deleterious side effects in light of the severity of the disease and necessity of the treatment. However, salts of acids and bases which are non-pharmaceutically acceptable may also find use, for example, in the preparation or purification of a pharmaceutically acceptable compound. All salts, whether pharmaceutically acceptable or not are included within the scope of the present invention.

The pharmaceutically acceptable acid and base addition salts as mentioned hereinabove are meant to comprise the therapeutically active non-toxic acid and base addition salt forms which the compounds as disclosed herein are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic and the like acids.

Conversely said salt forms can be converted by treatment with an appropriate base into the free base form.

Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

As defined in the background section, a Spinal Cord Injury (SCI) is defined as any injury, wound, or damage to the spinal cord that results in a loss of function, such as mobility or feeling. Frequent causes of damage are trauma (e.g., by car accident, gunshot, falls, etc.) or disease (polio, spina bifida, Friedreich's Ataxia, etc.). The spinal cord does not have to be severed in order for a loss of functioning to occur. In most individuals with SCI, the spinal cord is intact, but the damage results in loss of function. Besides a loss of sensation or motor function, individuals with SCI may also experience symptoms, conditions, or impairments including dysfunction of the bowel and bladder, sexual and fertility dysfunction, inability to regulate blood pressure effectively, reduced control of body temperature, inability to sweat below the level of injury, and chronic pain. A patient with SCI can have any level of SCI, as typically defined by the level of the damage (e.g., at or below any of the eight cervical vertebrae or the twelve thoracic vertebrae). Very high injuries (C-1, C-2) can result in a loss of many involuntary functions including the ability to breathe, necessitating breathing aids such as mechanical ventilators or diaphragmatic pacemakers.

Also as defined above, a Traumatic Brain Injury (TBI) (also termed as intracranial injury) is defined as any injury, wound, or damage caused by any type of trauma to the head, such as impact to the head or shaking. More specifically, TBI is an acquired injury to the brain caused by an external physical force, resulting in total or partial functional disability or psychosocial impairment, or both. The term applies to open and closed head injuries resulting in impairments in one or more areas, such as cognition; language; memory; attention; reasoning; abstract thinking; judgment; problem-solving; sensory, perceptual, and motor abilities; psychosocial behavior; physical functions; information processing; and speech. The term typically does not apply to brain injuries that are congenital or degenerative, or brain injuries induced by birth trauma, although the latter type of trauma may also be treated using the method of the invention. TBI can result in a variety of physiological and psychological symptoms, conditions or impairments, including physical impairments (e.g., speech, vision, hearing and other sensory impairment; headaches; lack of fine motor coordination; spasticity of muscles; paresis or paralysis of one or both sides and seizure disorders; balance impairments; and other gait impairments), cognitive impairments (e.g., short- and long-term memory deficits, impaired concentration, slowness of thinking and limited attention span, as well as impairments of perception, communication, reading and writing skills, planning, sequencing, and judgment), and psychosocial-behavioral-emotional impairments (e.g., fatigue, mood swings, denial, self-centeredness, anxiety, depression, lowered self-esteem, sexual dysfunction, restlessness, lack of motivation, inability to self-monitor, difficulty with emotional control, inability to cope, agitation, excessive laughing or crying, and difficulty relating to others).

In another embodiment, the maresins, i.e maresin-1 or maresin-2, preferably maresin-1, alone or combined with at least one specialized pro-resolving lipid mediator selected from other maresin, resolvin D1, resolving D2, resolving D3, resolvin D4, resolvin E1, resolvin E2, protectin D1, neuroprotection D1, lipoxin A4 and aspirin-triggered lipoxin, for use, according to any of the preceding embodiments, is included in a composition. In a preferred embodiment, said composition is formulated as a cosmetic composition, pharmaceutical composition, food formula, food ingredient or supplement, functional food, nutritional supplement, nutraceutical composition or is in the extract of a natural product. In a more preferred embodiment, said composition is a pharmaceutical composition. In another more preferred embodiment, said composition is a food. Note that if maresin-2 is used as a main compound, this can also be combined with at least maresin-1.

A composition of a "food" or "food ingredient or supplement", "functional food" or "nutritional supplement" as described above may in principle take any form suited for consumption by man or animal.

In addition, the composition comprising maresins, preferably maresin-1, alone or combined with at least one specialized pro-resolving lipid mediator selected from other maresin, resolvin D1, resolving D2, resolving D3, resolvin D4, resolvin E1, resolvin E2, protectin D1, neuroprotection D1, lipoxin A4 and aspirin-triggered lipoxin, might contain other ingredients. For example, the composition is mixed, dissolved, emulsified (e.g., in oil/water, water/oil, or double emulsions), or suspended in a matrix or base. The matrix or base can, e.g., be an edible oil such as ω-3 PUFA-containing oils, a ω-3 PUFA concentrate containing high levels of EPA, or DELA, or mixtures of EPA and DELA, or another edible oil suitable for consumption or administration. The matrix or base might also be water or an aqueous buffer. The composition might also be prepared in liposomes, nanoparticles, or microparticles.

To enhance shelf life, the compositions might also contain one or more stabilizers including antioxidants such as one or several tocopherols, ascorbic acid and ascorbyl-fatty acid derivatives, and other antioxidants which are commonly used in the stabilization of dietary oils, such as rosemary extract. The composition might furthermore be packaged in containers that minimize exposure to oxygen, heat, and incident light. These conditions will specifically augment the stability of maresins, preferably maresin-1, alone or combined with at least one specialized pro-resolving lipid mediator selected from other maresin, resolvin D1, resolving D2, resolving D3, resolvin D4, resolvin E1, resolvin E2, protectin D1, neuroprotection D1, lipoxin A4 and aspirin-triggered lipoxin, by preventing or limiting oxidation and isomerization of double bonds. Stability of the bulk oil or the formulated oil will also benefit from these conditions since the maresins, preferably maresin-1, alone or combined with at least one specialized pro-resolving lipid mediator selected from other maresin, resolvin D1, resolving D2, resolving D3, resolvin D4, resolvin E1, resolvin E2, protectin D1, neuroprotection D1, lipoxin A4 and aspirin-triggered lipoxin, are dissolved in oils with a significant level of PUFA that are sensitive to oxidation.

The compositions might also include one or more active ingredients such as aspirin, other non-steroidal anti-inflammatory drugs, vitamins, anti-oxidants, flavonoids, minerals, trace elements, fatty acids, lycopene, S-adenosylmethionine, oleocanthal, resveratrol, pterostilbene, bioactive proteins and peptides such as bromelain, oligosaccharides, glucosinolates, and plant extracts such as *Boswellia serrata*, mangosteen, capsicum, turmeric, ginger, tea, neem, and/or willow bark extract. Ingredients are not limited to the here mentioned examples.

Specific nutritional supplements can be made to support specific health conditions that include a fish oil, a krill oil, or a long-chain ω-3 PUFA concentrate supplemented with a composition comprising maresins, preferably maresin-1, alone or combined with at least one specialized pro-resolving lipid mediator selected from other maresin, resolvin D1, resolving D2, resolving D3, resolvin D4, resolvin E1, resolvin E2, protectin D1, neuroprotection D1, lipoxin A4 and aspirin-triggered lipoxin, together with glucosamine and chondroitin for arthritis, or with zinc, lutein and zeaxanthin for eye health.

Other nutritional supplements comprising maresins, preferably maresin-1, alone or combined with at least one specialized pro-resolving lipid mediator selected from other maresin, resolvin D1, resolving D2, resolving D3, resolvin D4, resolvin E1, resolvin E2, protectin D1, neuroprotection D1, lipoxin A4 and aspirin-triggered lipoxin, are multi-vitamin preparations, sports nutrition, fortified fish oil capsules, oral healthcare products such as tooth paste and mouthwash, and specific oils used as food such as spreads, dressings, cooking oils, snacks, nutritional drinks, soft gels, chewing gums, and in infant formulas.

Nutraceuticals can be defined as natural products that are used to supplement the diet by increasing the total dietary intake of important nutrients. This definition includes nutritional supplements such as vitamins, minerals, herbal extracts, antioxidants, amino acids, and protein supplements. Nutraceutical products fit into the newly created product category of "Dietary Supplements" as established by the F.D.A. in the Dietary Supplement Act of 1994. This act specifically defined dietary supplements to include: vitamins, minerals, herbs or other botanicals, antioxidants, amino acids, or other dietary substances used to supplement the diet by increasing the total daily intake. A "nutraceutical composition" is defined herein as a food composition fortified with ingredients capable of producing health benefits. Such a composition in the context of the present invention may also be indicated as foods for special dietary use; medical foods; and dietary supplements. For example, the food item or supplement may help to prevent or reduce symptoms associated with an inflammatory condition such as allergies (e.g. hay fever) and the like. As with the pharmaceutical composition, the amount of active ingredient in the food or food additive will depend on several factors. The food product will generally comprise a concentration that is sufficient to provide a consumer with an effective amount of active ingredient upon consumption of a regular (e.g. daily) portion of the food product. It will be recognized by those skilled in the art that the optimal quantity and spacing of individual dosages for achieving the therapeutic effects of the pharmaceutical composition, food item or food supplement described herein may easily be determined by the skilled person.

Dose ranges of the pharmaceutical compositions can be adjusted as necessary for the treatment of individual patients and according to the specific condition treated. Any of a number of suitable pharmaceutical formulations may be utilized as a vehicle for the administration of the compositions of the present invention and maybe a variety of administration routes are available. The particular mode selected will depend of course, upon the particular formulation selected, the severity of the disease, disorder, or condition being treated and the dosage required for therapeutic efficacy.

The composition comprising maresins, preferably maresin-1, alone or combined with at least one specialized pro-resolving lipid mediator selected from other maresin, resolvin D1, resolving D2, resolving D3, resolvin D4, resolvin E1, resolvin E2, protectin D1, neuroprotection D1, lipoxin A4 and aspirin-triggered lipoxin, for use, according to any of the preceding embodiments, is to be administered, but not limited thereto, by oral, rectal, topical, vaginal, parenteral (e.g., subcutaneous, intramuscular, intradermal, inhalation or intravenous), intrathecal, transdermal, intraperitoneal, and intrapulmonary and intranasal route. Preferably, said composition is to be administered by oral or parenteral route, although the most suitable route in any given case will depend on the nature and severity of the condition being treated and on the nature of the particular active product used.

Formulations suitable for oral administration may be presented in discrete units, such as capsules, cachets, lozenges, drops, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above).

In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations of the present invention suitable for parenteral administration conveniently comprise sterile aqueous preparations of the active compound, which preparations are preferably isotonic with the blood of the intended recipient. These preparations may be administered by means of subcutaneous, intravenous, intramuscular, inhalational or intradermal injection. Such preparations may conveniently be prepared by admixing the compound with water or a glycine buffer and rendering the resulting solution sterile and isotonic with the blood.

Formulations of the present invention are particularly suitable for topical application to the skin and preferably take the form of an ointment, cream, lotion, paste, gel, spray, aerosol, or oil. Carriers which may be used include Vaseline, lanoline, polyethylene glycols, alcohols, transdermal enhancers, and combinations of two or more thereof.

Formulations suitable for transdermal administration may also be presented as medicated bandages or discrete patches adapted to remain in intimate contact with the epidermis of the recipient for a prolonged period of time. Formulations suitable for transdermal administration may also be delivered by iontophoresis (passage of a small electric current to "inject" electrically charged ions into the skin; also called electromotive drug administration (EMDA)) through the skin.

The present invention also relates to a method of treating CNS injuries, in a subject, preferably a human subject, comprising administering to said subject a therapeutically effective amount of maresins, preferably maresin-1, alone or combined with at least one specialized pro-resolving lipid mediator selected from other maresin, resolvin D1, resolving D2, resolving D3, resolvin D4, resolvin E1, resolvin E2, protectin D1, neuroprotection D1, lipoxin A4 and aspirin-triggered lipoxin.

The present invention also relates to a method of treating spinal cord injury as defined above, in a subject, preferably a human subject, comprising administering to said subject a therapeutically effective amount of maresins, preferably maresin-1, alone or combined with at least one specialized pro-resolving lipid mediator selected from other maresin, resolvin D1, resolving D2, resolving D3, resolvin D4, resolvin E1, resolvin E2, protectin D1, neuroprotection D1, lipoxin A4 and aspirin-triggered lipoxin.

The present invention further relates to a method of treating traumatic brain injury as defined above, in a subject, preferably a human subject, comprising administering to said subject a therapeutically effective amount of maresins, preferably maresin-1, alone or combined with at least one specialized pro-resolving lipid mediator selected from other maresin, resolvin D1, resolving D2, resolving D3, resolvin D4, resolvin E1, resolvin E2, protectin D1, neuroprotection D1, lipoxin A4 and aspirin-triggered lipoxin.

The present invention also relates to a method of treating CNS injuries in a subject comprising administering to said subject, preferably a human subject, a therapeutically effective amount of a composition comprising maresins, preferably maresin-1, alone or combined with at least one specialized pro-resolving lipid mediator selected from other maresin, resolvin D1, resolving D2, resolving D3, resolvin D4, resolvin E1, resolvin E2, protectin D1, neuroprotection D1, lipoxin A4 and aspirin-triggered lipoxin.

The present invention also relates to a method of treating spinal cord injury as defined above in a subject comprising administering to said subject, preferably a human subject, a therapeutically effective amount of a composition comprising maresins, preferably maresin-1, alone or combined with at least one specialized pro-resolving lipid mediator selected from other maresin, resolvin D1, resolving D2, resolving D3, resolvin D4, resolvin E1, resolvin E2, protectin D1, neuroprotection D1, lipoxin A4 and aspirin-triggered lipoxin.

The present invention also relates to a method of treating traumatic brain injury as defined above, in a subject, preferably a human subject, comprising administering to said subject a therapeutically effective amount of a composition comprising maresins, preferably maresin-1, alone or combined with at least one specialized pro-resolving lipid mediator selected from other maresin, resolvin D1, resolving D2, resolving D3, resolvin D4, resolvin E1, resolvin E2, protectin D1, neuroprotection D1, lipoxin A4 and aspirin-triggered lipoxin.

The phrase "therapeutically effective amount" means the amount of such a substance that produces some desired local or systemic effect at a reasonable benefit/risk ratio applicable to any treatment. The therapeutically effective amount of such substance will vary depending upon the subject and disease condition being treated, the weight and age of the subject, the severity of the disease condition, the manner of administration and the like, which can readily be determined by one of ordinary skill in the art. For example, certain compositions of the present disclosure may be administered in a sufficient amount to produce a reasonable benefit/risk ratio applicable to such treatment.

It should be noted that all the previous embodiments can be practiced independently from each other or combined with any other embodiment disclosed herein.

The present invention will be now further illustrated by reference to the following examples which do not intend to limit the scope of the present invention.

Examples

Material and Methods

Spinal Cord Contusion Injury and Maresin-1 (MaR1) Treatment

All surgical procedures were approved by the Universitat Autònoma de Barcelona Animal Care Committee and followed the guidelines of the European Commission on Animal Care, and the methods for each procedure were carried out in accordance with the approved guidelines. 142 Adult (8 to 10 weeks old) female C57Bl/6 mice (Charles River) were anesthetized with ketamine:xylazine (90:10 mg/kg). After performing a laminectomy at the 11th thoracic vertebrae, the exposed spinal cord was contused using the Infinite Horizon Impactor device (Precision Scientific Instrumentation, Lexington, Ky.). Injuries were made using a force of 60 kdynes and tissue displacement ranging between 500-700 µm as reported earlier (Coll-Miro et al., 2016).

One hour after spinal cord injury, 1 µg of MaR1 (7S,14S-dihydroxy-4Z,8E,10E,12Z,16Z, 19Z-docosahexaenoic acid; Cayman Chemical) was injected intravenously in 100 µl of sterile saline, and then repeated daily thereafter until day 7. Control mice were injected with an equal volume of sterile saline following the same injection protocol. Precautions with regards to the handling of lipid mediators to prevent inactivity due to oxygenation were implemented. The MaR1 dosage was chosen accordingly to be above levels i) of approved MaR1 bioactivity in experimental disease models (Serhan et al., 2015) and ii) above SPM dosages sufficient to exert bioactivity in the CNS with intact and closed blood brain barrier (Marcheselli et al., 2003; Svensson et al., 2007).

Flow Cytometry

Immune cells from the laminectomized and injured spinal cord were analyzed by flow cytometry at 1, 3, 7, 14, 21 and 28 days post-injury as described previously to study the dynamics of immune cell in spinal cord injury as described previously (Santos-Nogueira et al., 2015; Coll-Miro et al., 2016; Francos-Quijorna et al., 2016). Similarly, spinal cord from mice treated with MaR1 or saline were also harvested at day 1, 3 and 7 post-lesion. Briefly, spinal cords were cut in little pieces and passed through a cell strainer of 70 µm (BD falcon) and the cell suspension was centrifuged twice at 300 g for 10 minutes at 4° C. After cell counts, samples were divided, and cells alone and isotype-matched control samples were generated to control for nonspecific binding of antibodies and for auto-fluorescence. The following antibodies from eBioscience were used at 1:250 concentration: CD45-PerCP, CD11b-PE-Cy7, Ly6C-FITC, Ly6G-PE, Gr1-FITC, F4/80-APC or PE, CD3-FITC, CD4-APC, CD8-APC, CD19-PE, CD206-FITC, CD16/32-PE. After 30 min of incubation with combinations of antibodies at 4° C., cells were then fixed in 1% paraformaldehyde. For intracellular staining, cells were permeabilized with Permeabilization Wash Buffer (Biolegend), incubated with unconjugated rabbit antibodies against iNOS (1:200 Abcam), and goat antibodies against Arg1 (1:200; Santa Cruz) for 30 minutes, followed by staining with Alexa488 or Alexa647 conjugated donkey secondary antibodies against rabbit or goat (1:500 Molecular Probes) for 30 min. Finally, samples were washed and fixed in 1% paraformaldehyde. To perform the analysis, cells were first gated for CD45 to ensure that only infiltrating leukocytes and resident microglia are selected. Then, the following combination of markers were used to identify: microglia ($CD45^{low}$, $CD11b^+$, $F4/80^+$); macrophages ($CD45^{high}$, $CD11b^+$, $F4/80^+$); neutrophils ($CD45^{high}$, $CD11b^+$, $F4/80^-$, $Gr1^{high}$); CD4 T-Cells ($CD45^+$, $CD11b^-$, $CD3^+$, $CD4^+$); CD8 T Cells ($CD45^+$, CD11b, $CD3^+$, $CD8^+$); B cell ($CD45^+$, $CD11b^-$, $CD3^-$, $CD19^+$). To study the phenotype of microglia and macrophages, these cells were further differentiated based on Ly6C, CD16/32, iNOS, CD206 and Arg1 expression (Coll-Miro et al., 2016; Francos-Quijorna et al., 2016). Analysis of inflammatory cell kinetics at the lesion site was conducted applying objective and quantifiable measures of resolution dynamics as described previously (Pruss et al., 2011). Cells were analyzed using FlowJo® software on a FACSCanto flow cytometer (BD Biosciences).

Lipid Mediator Lipidomics

A 5 mm segment of uninjured and contused spinal cord centered on the lesion tissue was harvested at 1, 3, 7 and 14 days post-injury for LC-MS/MS. Briefly, For endogenous lipid autacoid analysis, frozen spinal cords were homogenized with a hand-held tissue grinder in 66% methanol (4° C.). Homogenized tissue samples were combined with two volumes of methanol (4° C.). The methanol contained deuterated internal standards, PGE2-d4, LXA4-d5, leukotriene B4 ($LTB_4$-d4), 15(S)-hydroxyeicosatetraenoic acid [15(S)-HETE-d8], AA-d8) and DHA-d54 (400 pg/each), to calculate recovery of different classes of oxygenated fatty acids and PUFA. Lipid autacoids were extracted by solid phase using Accubond ODS-C18 cartridges (Agilent Technologies, Santa Clara, Calif.). Eicosanoids, docosanoids and PUFA were identified and quantified by LC/MS/MS-based lipidomics (Hassan and Gronert, 2009; Pruss et al., 2013). In brief, extracted samples were analyzed by a triple quadruple linear ion trap LC/MS/MS system (MDS SCIEX 3200 QTRAP) equipped with a LUNA C18-2 mini-bore column using a mobile phase (methanol:water:acetate, 65:35:0.02, v:v:v) with a 0.50 ml/flow rate. MS/MS analyses were carried out in negative ion mode and hydroxy fatty acids were quantified by multiple reaction monitoring (MRM mode) using established transitions. Calibration curves (1-1000 pg) and specific LC retention times for each compound were established with synthetic standards (Cayman Chemical, Ann Arbor, Mich.).

Cytokine Protein Expression

Mice treated with saline or MaR1 were perfused with sterile saline and a 5 mm length of spinal cord centered on the lesion was collected at 12 and 24 h after contusion injury and snap-frozen. Spinal cords were homogenized and protein concentration was determined using the DC Protein Assay (Bio-Rad). Samples were concentrated to 4 µg/µl using MicroCon centrifugation filters (Millipore) to ensure equal amounts of protein. Low concentrations of cytokines in the sample result in binding to the filters whereas high concentrations of protein sustain less losses. The protein levels of 32 cytokines and chemokines were then analyzed using the Milliplex MAP Mouse Cytokine/Chemokine magnetic bead panel (Millipore) on a Luminex (Millipore) as per manufacturers' protocol (Francos-Quijorna et al., 2016).

Western Blotting

Samples used for Luminex assay, were also used to for western blotting. Protein samples (30 µg) were separated by electrophoresis on a 10-15% polyacrylamide gel and transferred onto PVDF membranes (Millipore). The membranes were incubated overnight at 4° C. with rabbit antibodies against phospho NF-kB p65 (1:1000; Cell Signaling), against the phosphorylated form of STAT1 (1:500; Cell Signaling), STAT3 (1:500; Cell Signaling), STAT5 (1:500; Cell Signaling) and STAT6 (1:500; Cell Signaling), JNK (1:500; Santa Cruz), ERK1/2 (1:1000; Cell Signaling), p38 (1:1000; Cell Signaling) and AKT (1:1000; Cell Signaling). Bands were detected using Chemiluminescence (Immobilon Western Chemiluminescence HRP reagent, Millipore) and data quantified by densitometry using Workflow v3 software in a Chemidoc apparatus (Millipore). ß-actin (1:10.000; Sigma Aldrich) was used to ensure equal loading of samples.

Functional Assessment

Locomotor recovery was evaluated at 1, 3, 5, 7, 10, 14, 21 and 28 dpi in an open-field test using the nine-point Basso Mouse Scale (BMS) (Basso et al., 2006), which was specifically developed for locomotor testing after contusion injuries in mice. The BMS analysis of hindlimb movements and coordination was performed by two independent assessors blinded for the treatment groups (MaR1 vs saline) and the consensus score taken. In addition, at the end of the follow up (day 28 post-injury), a computerized assessment of locomotion was also performed using the DigiGait™ Imaging System (Mouse Specifics, Inc.). This system consists of a motorized transparent treadmill belt and a high-speed digital video camera that captures images of the paws from the underside of the walking animals. DigiGait™ software generates "digital pawprints" and dynamic gait signals, representing the temporal record of paw placement relative to the treadmill belt. This locomotor test allows for an easy and objective analysis of both static and dynamic locomotor parameters. Moreover, the highest locomotion speed that each mouse was to able locomote for at least 5 seconds was also recorded on the DigiGait treadmill belt. Functional tests were done blinded to the experimental groups.

Histology

At 28 days post-injury, mice were perfused with 4% paraformaldehyde in 0.1M-phosphate buffer (PB). A 5 mm length of spinal cord containing the lesion site was removed, cryoprotected with 30% sucrose in 0.1M PB at 4° C., and 10 series of 10 µm thick section were picked up on glass slides. Adjacent sections on the same slide were therefore 100 µm apart. For quantification of myelin area content in the spinal cord analyses, sections were stained with Luxol Fast Blue (Sigma). For neuronal and axonal assessment, sections were incubated overnight at 4° C. with biotinylated antibodies against NeuN (1:200, Millipore) and NF (1:1000, Millipore), respectively. Double immunostaining for NF and MBP (1:100; Abcam) was done to assess the sparing of myelinated axons. Sections were incubated for 1 hour at room temperature with the streptavidin-Alexa 594 conjugated or donkey anti-rabbit Alexa 594-conjugated antibodies (Molecular Probes, 1:500), and then coverslipped in Mowiol containing DAPI to label nuclei.

The epicenter of the injection or contusion injury impact was determined for each mouse spinal cord by localizing the tissue section with the greatest damage using LFB stained section. Myelin content after SCI was calculated by delineating the are of LFB stained tissue. Neuronal survival was assessed by counting the number of NeuN$^+$ cells in the ventral horns at the injury epicenter and at rostral and caudal areas. Axonal sparing was calculated by counting the number of axons in the dorsal column at the injury epicenter, the region of most pronounced damage. The same sections were used to examine axonal demyelination in the dorsal column through counting the fibers double stained for NF and MBP at the lesion epicenter. All quantifications were performed blinded to the experimental groups with the help of the ImageJ image analysis software.

Statistical Analyses

Data are shown as mean±standard error of the mean (SEM). Kolmogorov-Smirnov test was used to test normality. Dependent on data being normal on non-normal distributed we chose parametric or non-parametric tests. Dynamics of immune cell recruitment and lipidomic profile after SCI were analyzed by using one-way ANOVA with post-hoc Bonferroni's test. Functional follow-up for BMS score and subscore, as well as histological analysis of myelin and neuronal sparing were analyzed using two-way repeated measure ANOVA with post-hoc Bonferroni's post-hoc test for multiple comparisons. Two-tailed Student's or the non-parametric Mann-Whitney's test was used for single comparison between two groups, and one-way ANOVA followed by Dunnett's multiple post hoc test for comparing more than two groups. Maximal speed on a treadmill was analyzed using the Mantel-Cox test. Differences were considered significant at $p<0.05$.

Results

Inflammatory Cell Clearance is Impaired after SCI

We first evaluated, by flow cytometry, the dynamics of the main inflammatory cell types in the contused spinal cord of C57/Bl6 mouse and assessed different parameters to characterize the inflammatory resolution and to determine the persistence of the different immune cell subpopulations at the lesion site after spinal cord contusion in mice. We detected that the accumulation of neutrophils, macrophages and microglia cell reached maximal cell numbers in the contused spinal cord at day 1, 3 and 7 post-injury, respectively (FIG. 1A-C). Subsequently their numbers dropped progressively up to day 7-14 post-injury, remaining at high and steady levels up to day 28 (FIG. 1A-C). The resolution index ($R_i$; time window between time-point of maximum cell numbers to a reduction by 50%) of neutrophils and macrophages was 2.5 and 9.5 days, respectively, reflecting the slower clearance of macrophages in SCI as compared to neutrophils. Microglia $R_i$ could not be calculated owing to the rapid decline in their cell counts from 7 to 14 days post-injury, however, this is lower than 7. We then quantified the resolution plateau ($R_p$: percent of persistent cellular component relative to max cell numbers) to provide quantitative measurements of the inflammatory resolution after SCI (Pruss et al., 2011). $R_p$ revealed the clearance of all three myeloid cell subsets after SCI was incomplete, with ~35% remaining neutrophils, macrophages and microglial cells at day 28 following lesion (FIG. 1A-C).

We also studied the recruitment of lymphocytes in the contused spinal cord. We observed infiltration of B cells and T cells, both CD4$^+$ and CD8$^+$ lymphocytes, during the first few days after contusion injury, but at much lower numbers as compared to monocytes (FIG. 1D-F). $R_p$ of the different lymphocyte subsets was >50% at day 28, indicating the persistent presence of lymphocytes in SCI exposed to CNS antigens throughout. These results provide clear evidence that immune cells are not efficiently eliminated from the contused spinal cord and highlight that the resolution capacity of the injured spinal cord is impaired after SCI.

Figure 2:
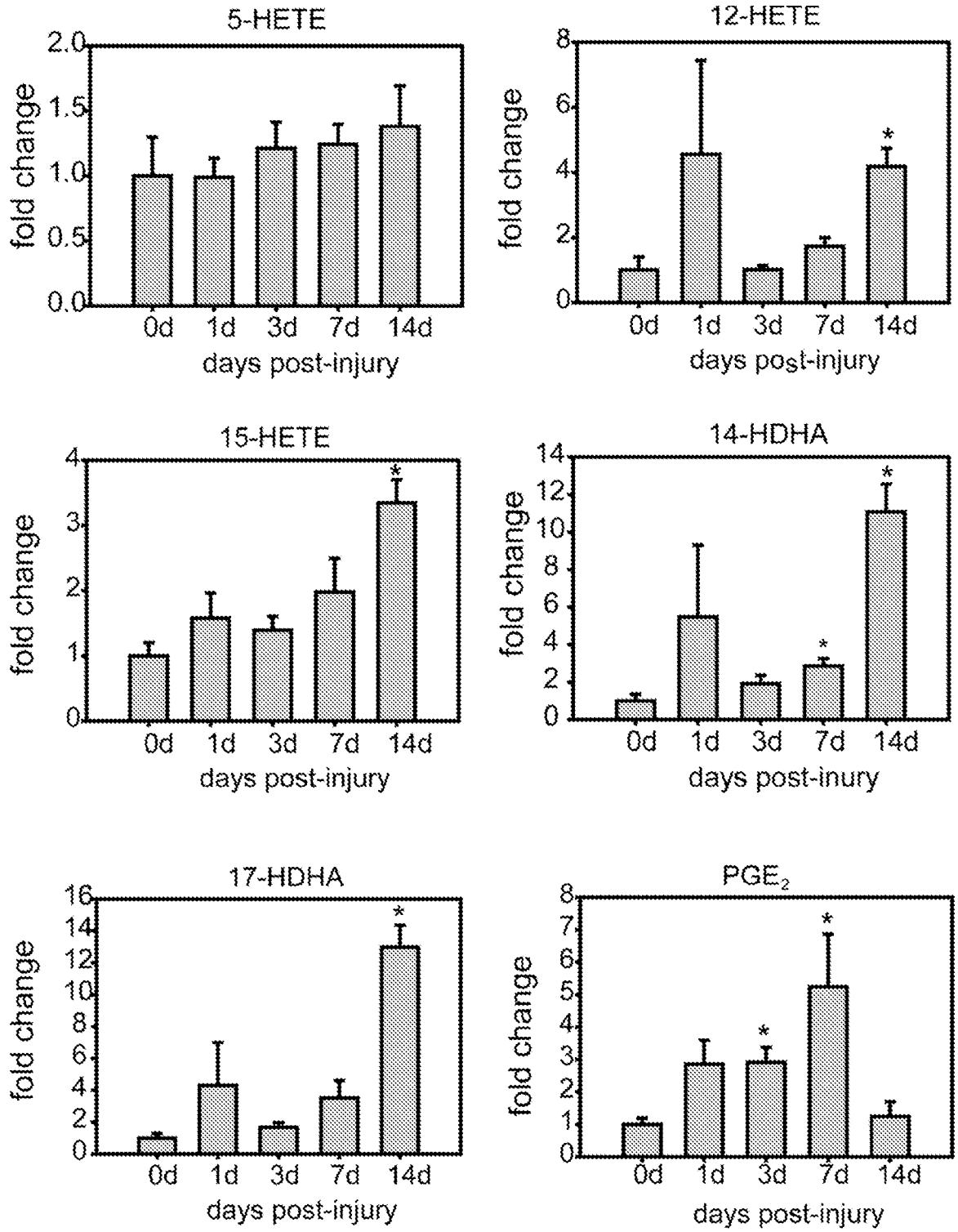
FIG. 2. Impaired and delayed synthesis of pro-resolving lipid mediators after SCI. Resolution metabolome profiles after SCI were analyzed using LC-MS-MS of whole spinal cord lysates. Pro-inflammatory eicosanoid profiles indicated by $PGE_2$ levels follow closely the formation of inflammation with an early increase at day 1 and mounts to peak at day 7 followed by a drop until day 14. This time-point marks a switch in the lipid mediator biosynthesis profile demarcated by starting increase of the pro-resolution pathways. Both the MaR1 and PD1 synthesis commences not before 2 weeks after SCI indicated by 10-13-fold increase of the pathway markers such as 14-HDHA (MaR1) or 17-HDHA (PD1). This is further matched by the weak and late induction of 5-HETE, 12-HETE and 15-HETE indicative for the biosynthesis of the SPM Lipoxin $A_4$. *p<0.05 vs uninjured spinal cords (0d). One Way ANOVA with Tukey's post hoc correction (n=4 per point). Error bars indicate SEM.

Defective Lipid Mediator Class Switch as a Classical Hallmark of Impaired Resolution in Acute SCI Lesions We investigated whether the impaired clearance of inflammatory cells is mirrored by failed induction of synthesis of specialized pro-resolution mediators (SPM), which have been identified as crucial for efficient resolution (Serhan, 2014). Lipidomic analysis of spinal cord revealed delayed synthesis of SPM after contusion injury. The levels of 12-HETE and 15-HETE, which are pathway markers of the synthesis of the arachidonic acid (AA) derived SPMs known as lipoxin $A_4$ (LXA$_4$), did not increase until day 14 post-injury (FIG. 2). Levels of 5-HETE, however, did not change after injury (FIG. 2). Similarly, the synthesis of SPM derived from docosohexaenoic acid (DHA) was also delayed in SCI, since the levels of 17-HDHA, a pathway marker for the formation of resolvin D (RvD) and protectin D1 (PD1), and 14-HDHA, the precursor of maresin1 (MaR1), were not induced until day 14. Moreover, SPM derived from eicosopentaenoic acid (EPA) were also impaired after SCI, since 18-HEPE, the pathway marker for the formation of resolvin E (RvE) series, was undetected in the injured spinal cord for the time period analysed (14 days). Thus, the CNS lesion milieu is characterized by a defective and delayed induction of SPM, involving those derived from AA (omega-6), DHA and EPA (omega-3) pathways, which are required for orchestrating efficient resolution of inflammation. This inability to generate a resolution conducive milieu is contrasted by a full-blown early PGE2 response as a hallmark of pro-inflammatory activity (FIG. 2). These data indicate that the class switch from pro-inflammatory to pro-resolution lipid mediators derived from AA, DHA and EPA does not occur in the injured spinal cord.

MaR1 Regulates Resolution of Inflammation in the Injured Spinal Cord

Figure 3:
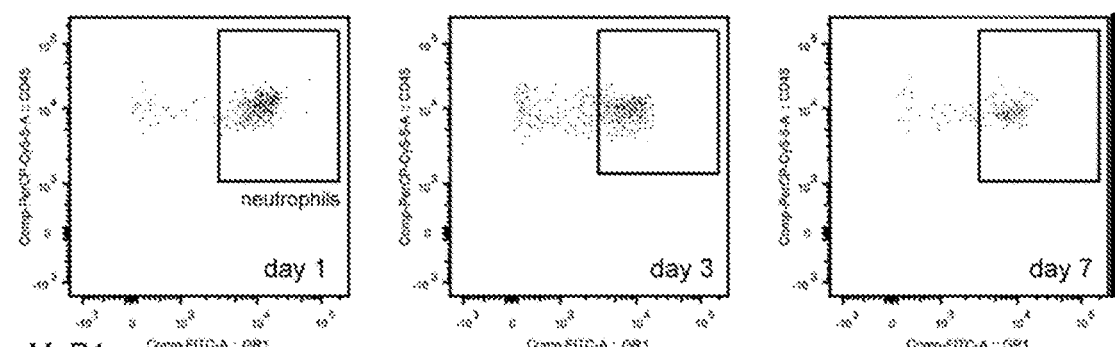
FIG. 3. MaR1 propagates the resolution of neutrophil inflammation. (A-B) Representative density plots of FACS analysis showing neutrophils at 1, 3 and 7 days after the injury in the spinal cord of saline (A) and MaR1 (B) treated mice. (C) Graph showing neutrophil recruitment and resolution indices. Note that MaR1 treatment (grey line) does not interfere with the proinflammatory cell infiltration but induces a more rapid decline of neutrophils. Insert shows some inflammatory kinetics measurement, which include: $\psi$max=maximal cell counts; $\psi$3 and $\psi$7=cell counts at day 3 and 7 post-injury; Tmax=time after SCI until reaching max cell numbers, T50=time after SCI until reduction of cell numbers by 50%, and Ri. *p<0.05 vs saline; Two Way ANOVA with Bonferroni's post hoc was used to analyze significant differences in the dynamics of neutrophil counts after SCI, and t-test was used to assess the different inflammatory kinetic indices. (n=6 per time point and group). Error bars indicate SEM.
Figure 3:
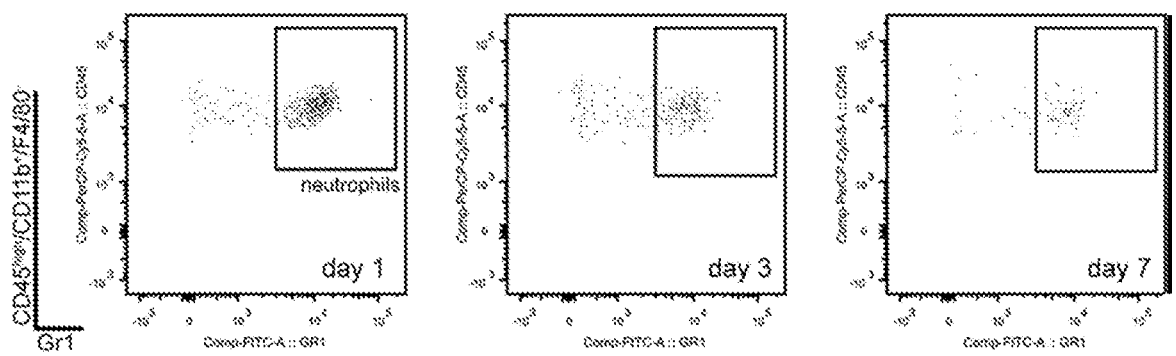
Figure 3:
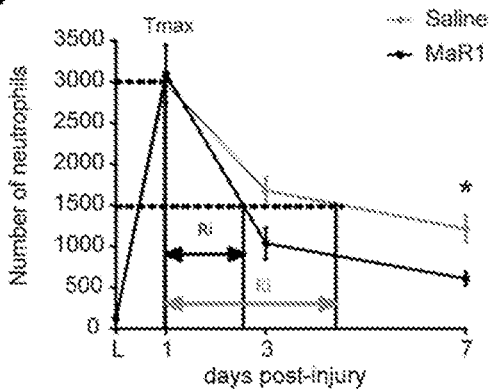
Figure 4:
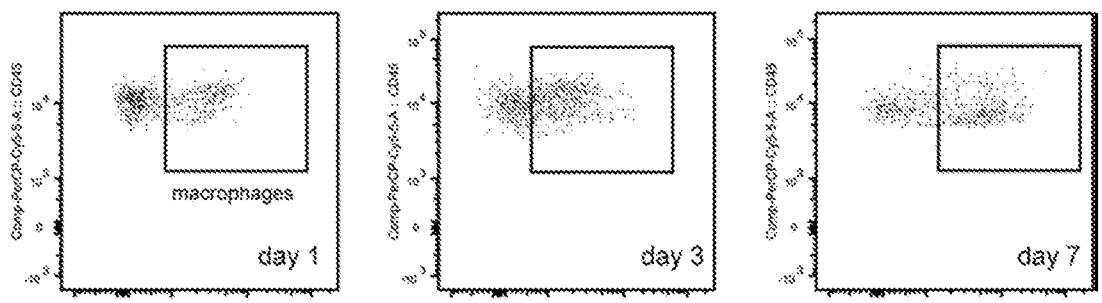
FIG. 4. MaR1 propagates late macrophages clearance from the lesion site. (A,B) Representative FACS analysis dot plots showing the dynamics of macrophages accumulation in the spinal cord at 1, 3 and 7 days after the injury in saline (A) and MaR1 (B) treated mice. (C-D) Graphs showing quantification of macrophage and microglial cells from FACS analysis. Note the reduced numbers of macrophages at day 7 after MaR1 treatment, demarcating the enhanced resolution plateau triggered by this SPM. However, microglial counts were not modulated by MaR1 for the first week post-injury. *p<0.05 vs saline; Two Way ANOVA with Bonferroni's post hoc was used to analyze significant differences. (n=6 per time point and group). Data are expressed as mean±SEM.
Figure 4:
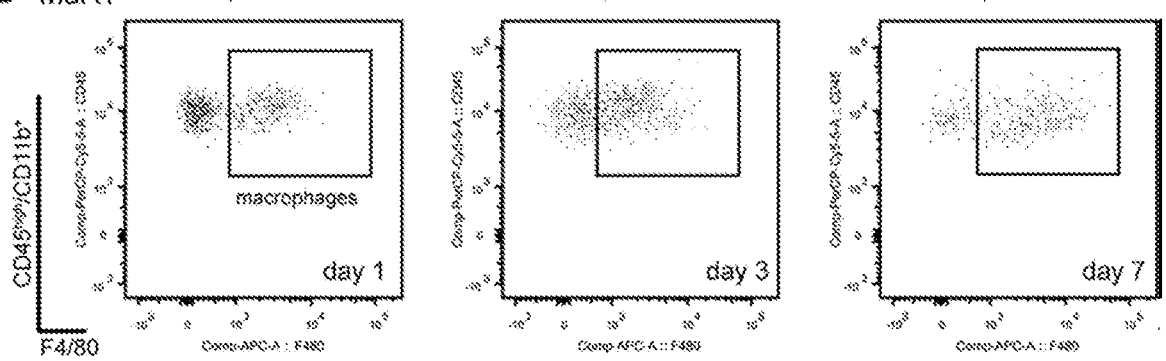
Figure 4:
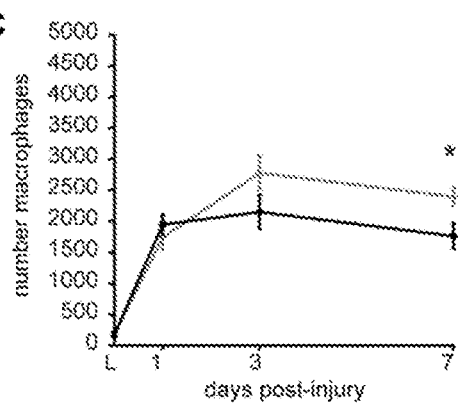
Figure 4:
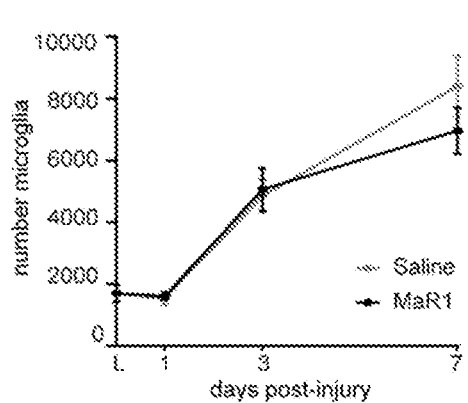

To assess whether the deficit in the resolution of inflammation after SCI is linked to impaired synthesis of SPM, we investigated whether systemic administration of the DHA-derived SPM coined MaR1 enhanced immune cell clearance from the contused spinal cord. Daily intravenous administration of MaR1 for 7 days starting 1 hour after SCI did not impede the infiltration of neutrophils into the contused spinal cord, as their counts at day 1 post-injury, when neutrophil accumulation peaks after SCI, were unaltered by MaR1 treatment (FIG. 3). However, MaR1 accelerated the clearance of neutrophils from the contused spinal cord, based on several resolutions parameters (Ri and $T_{50}$), and reduced ~50% the neutrophil counts in the injured spinal cord at day 7 (FIG. 3). We next studied whether MaR1 interfered with the recruitment of macrophages after SCI. The entrance of blood-borne macrophages into the contused spinal cord was not different at day 1 after MaR1 treatment (FIG. 4A-C), but tended to be reduced at day 3 post-injury, although not significantly. However, macrophage accumulation in the lesioned spinal cord was significantly reduced after MaR1 treatment at day 7 post-lesion (FIG. 4A-C). MaR1 treatment did not attenuate microglial numbers in the contused spinal cord during the first week following contusion injury, although it tended to be reduced at day 7 post-lesion upon administration of this SPM (FIG. 4D). These results provide clear evidence that systemic delivery of MaR1 enhances the elimination of peripheral myeloid cells (neutrophils and macrophages) from the injured spinal cord, suggesting an important role for MaR1 in promoting resolution of inflammation after SCI.

MaR1 Silences Cytokine Expression in SCI

In an attempt to assess the mechanisms underlying the resolving actions of MaR1 in SCI, we assessed changes in expression of cytokines at the protein level in the contused spinal cord by doing a Luminex assay. These experiments revealed that MaR1 treatment significantly reduced the levels of CXCL1, CXCL2, CCL3, CCL4, IL-6, and CSF3 (FIG. 5A; Table Si). In addition, the expression of IL-3, IL-13 and CXCL5, which were found at low levels in contused spinal cord of mice treated with vehicle, were undetectable in those treated with MaR1 (see Table 1 below). IL-4 protein levels were undetected in the injured spinal cord of both groups. Note that MaR1 did not reduce the protein levels of the anti inflammatory cytokine IL-10 after SCI (FIG. 5A), suggesting MaR1 preferably attenuates pro-inflammatory cytokines.

TABLE 1

Protein levels of citokines significantly silenced by MaR1 in SCI.

| | Naive | Saline | MaR1 |
| --- | --- | --- | --- |
| IL-3 | ND | 0.56 ± 0.03 | ND |
| IL-6 | 0.94 ± 0.03 | 671 ± 133 | 291 ± 56.7* |
| IL-13 | ND | 4.19 ± 1.38 | ND |
| CSF3 | ND | 1179 ± 182 | 741 ± 118* |
| CXCL1 | 2.81 ± 0.23 | 219 ± 67.6 | 87.5 ± 21.3* |
| CXCL2 | 4.59 ± 0.30 | 119 ± 17.9 | 41.4 ± 7.50* |
| CXCL5 | ND | 4.80 ± 0.86 | ND |
| CCL3 | ND | 21.5 ± 2.52 | 13.3 ± 1.18* |
| CCL4 | ND | 28.9 ± 3.47 | 17.7 ± 1.46* |

*$p < 0.05$ MaR1 vs Saline, ND = below limits of detection.

Figure 5:
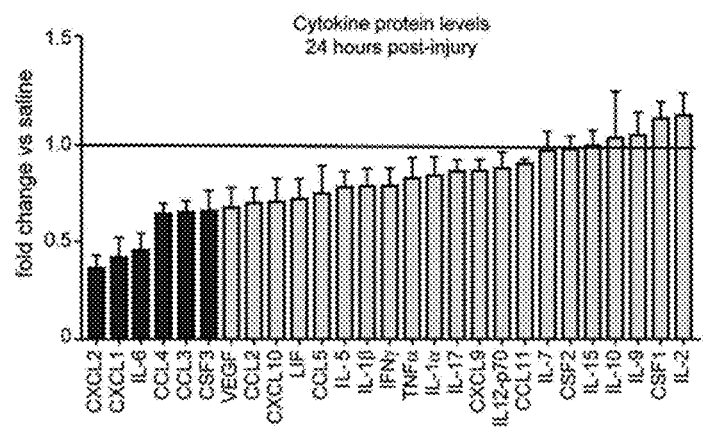
FIG. 5. Acute mechanistic signaling underlying systemic MaR1 treatment at the lesion site. (A) The cytokine protein level profile 24 h after MaR1 treatment is characterized by a reduced expression of chemokines (CXC12, CXCL1, CCL3, CCL4, CSF3), and the pro-inflammatory cytokineIL-6 (black bars) as indicated by Luminex analysis. (B) WB blot showing different inflammatory intracellular pathways in contused spinal cord at 24 h post-injury. Note that MaR1 treatment attenuated the activation of STAT-1, STAT-3, STAT-5, p38 and ERK1/2 signaling at the lesion site, but does not limit NF-κB and PI3K/Akt activation after SCI. *p<0.05 vs saline; One way ANOVA with Dunnet's post hoc test was used to analyze significant differences (n=3 in uninjured and contused saline-treated injured mice; n=4 in contused MaR1-treated mice). Data are expressed as mean±SEM.
Figure 5:
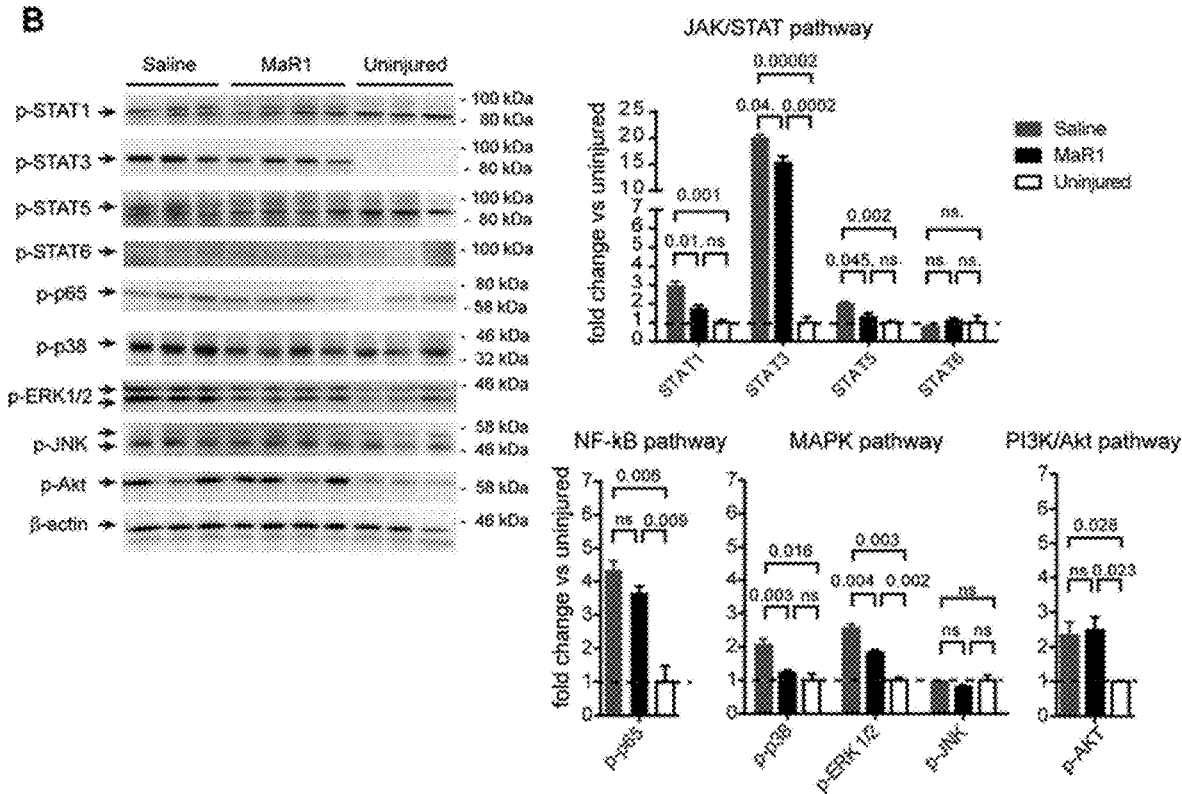

Since cytokines are regulated by multiple signal transduction pathways, we then investigated which of the main inflammatory signaling mechanisms were attenuated by MaR1 after SCI. Western blot analysis of spinal cord tissue taken 24 hours after SCI revealed that levels of pP65 and pAkt were up-regulated after contusion injury, but these levels were not affected by MaR1 treatment (FIG. 5B,C). In contrast, STAT and MAPK pathway, two of the main inflammatory signaling mechanisms, after SCI showed differences. Specifically, STAT1, STAT3 and STAT5, as well as p38 and ERK1/2, were significantly increased at 24 hours post-injury in saline treated mice, and all of them were attenuated upon MaR1 treatment (FIG. 5B,C). STAT6 and JKN, which were not significantly activated after SCI, remained unaltered after MaR1 administration. These data provide clear evidence that MaR1 silences cytokine expression and turns off the activation of some members of the STAT and MAPK pro-inflammatory signaling pathways, but does not limit NF-κB and PI3K/Akt signaling after SCI.

Actions of MaR1 on Microglia and Macrophage after SCI

Figure 6:
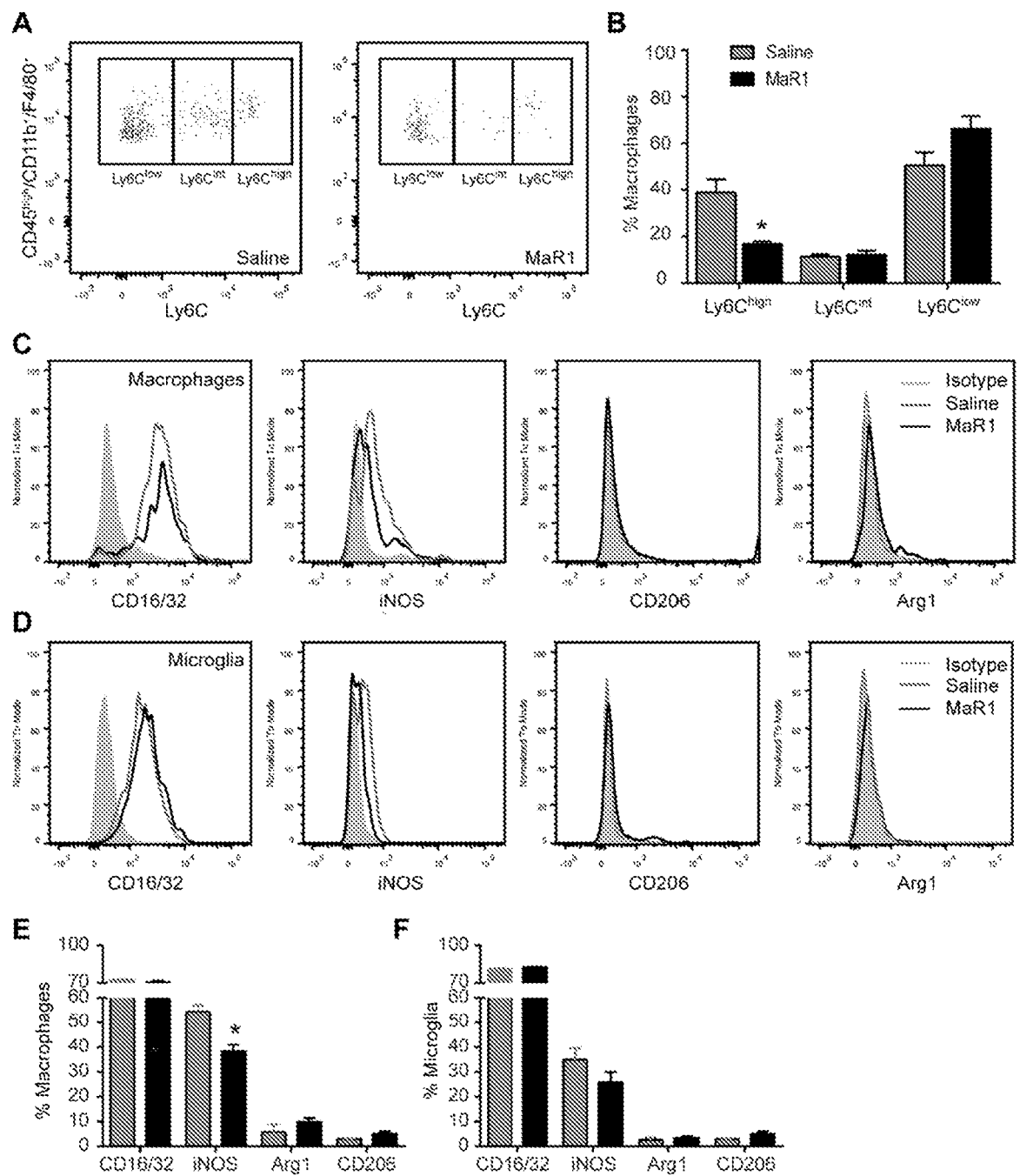
FIG. 6. MaR1 redirects macrophages towards a pro-repair phenotype after SCI. (A) Representative FACS analysis density plots of Ly6C macrophages in saline and MaR1 treated mice at day 7 post injury. (B) Graph showing proportion of different macrophage subsets in the injured spinal cord 7 days after the injury. (C-D) Representative FACS histograms plots of M1 and M2 markers in injured spinal cord for macrophages (C) and microglial cells (D) at 7 days post injury. (E-F) Graphs showing the quantification of macrophages (E) and microglial cells (F) expressing M1 and M2 markers after SCI. *p<0.05 vs saline. Student t-test was used to analyze significant differences between MaR1 and control mice. (n=6 per group). Data are expressed as mean±SEM.

Macrophages are a heterogeneous population of cells that exert divergent effects on damaged tissue depending on their phenotype. Ly6C$^{high}$ macrophages are pro-inflammatory macrophages and exhibit phagocytic, proteolytic functions, and mediate cytotoxicity. In contrast, Ly6C$^{low}$ (also known as LyC6$^{neg}$) macrophages are anti-inflammatory macrophages and promote wound healing and repair (Arnold et al., 2007; Nahrendorf et al., 2007). Since cytokines play a key role in regulating macrophage phenotype (David and Kroner, 2011; Kroner et al., 2014), we studied whether MaR1 modulated the proportion of Ly6C$^{high}$ and Ly6C$^{low}$ macrophages at 7 days after SCI, the time point when MaR1 treatment reduced the number of these cells. We found that MaR1 had a significant impact on macrophage phenotype based on Ly6C expression, since this SPM markedly reduced (~50%) the amount of pro-inflammatory macrophages (Ly6C$^{high}$) but not the anti-inflammatory macrophages (Ly6C$^{low}$) (FIG. 6A,B). Indeed, the ratio LyC6$^{low}$/LyC6$^{high}$ in saline treated SCI mice was 1.57±0.39. In contrast, this ratio was increased to 3.73±0.26 by MaR1 (p=0.0036 vs saline; t-test), highlighting that were almost 4 fold greater anti-inflammatory than pro-inflammatory macrophages in the spinal cord of mice treated with MaR1 (FIG. 6A,B).

This SPM also significantly reduced expression of the pro-inflammatory, cytotoxic enzyme iNOS (FIG. 6C,E) in macrophages. Moreover, MaR1 induced a ~2 fold increase of Arg-1 expression in macrophages, which was barely detectable in vehicle controls, although it did not reach statistical significance (FIG. 6C,E). Together, these data indicate that MaR1 converts the phenotype of macrophages in the injured spinal cord towards a more pro-repair and anti-inflammatory state.

In contrast to macrophages, most microglial cells were Ly6C$^{low}$ in SCI (~85%), and MaR1 did not reduce the percent of Ly6C$^{high}$ microglia (9.6%±0.8 and 10.6%±1.1, in saline- and MaR1-treated mice, respectively). MaR1 treatment tended to reduce the expression of iNOS, (FIG. 6D, F), although not to a statistically significant level. These results, therefore, suggest that the immunomodulatory effects of MaR1 after SCI are mostly related to macrophages but not microglia, at least up to day 7 post-injury.

Figure 7:
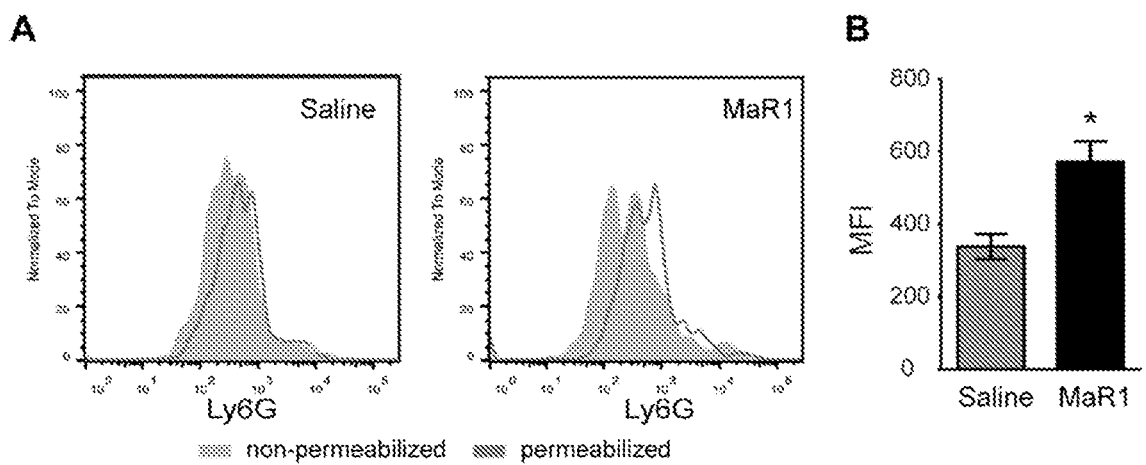
FIG. 7. MaR1 increases efferocytosis after SCI. (A) Representative FACS analysis histogram plots of the specific neutrophil marker Ly6G in macrophages at day 7 post-injury after saline or MaR1 treatment. (B) Bar plot shows the increased in Ly6G median fluorescence intensity (MFI) in macrophages when the cell membrane is permeabilized, which is indicative of neutrophil phagocytosis. Note that MaR1 increased ~2 fold the engulfment of neutrophils by macrophages. * $p<0.05$ vs saline; Mann-Whitney test used to analyze significant differences. (n=4 per group). Data are expressed as mean±SEM.

As phagocytosis of neutrophils by macrophages is a crucial step for the resolution of inflammation (Schwab et al., 2007; Serhan, 2014; Serhan et al., 2015), we monitored whether MaR1 increased the ability of macrophages to phagocytose neutrophils (efferocytosis). We found that the amount of the selective neutrophil marker Ly6G inside the macrophages (CD45$^{high}$, CD11b$^+$, F4/80$^+$) was increased ~2 fold in the spinal cords of mice treated with MaR1 at 7 days post-lesion, indicating that this SPM enhanced neutrophil phagocytosis in SCI (FIG. 7A, B). Therefore, exogenous administration of MaR1 drives macrophage activation towards a more restorative phenotype after SCI and enhances efferocytosis.

Figure 8:
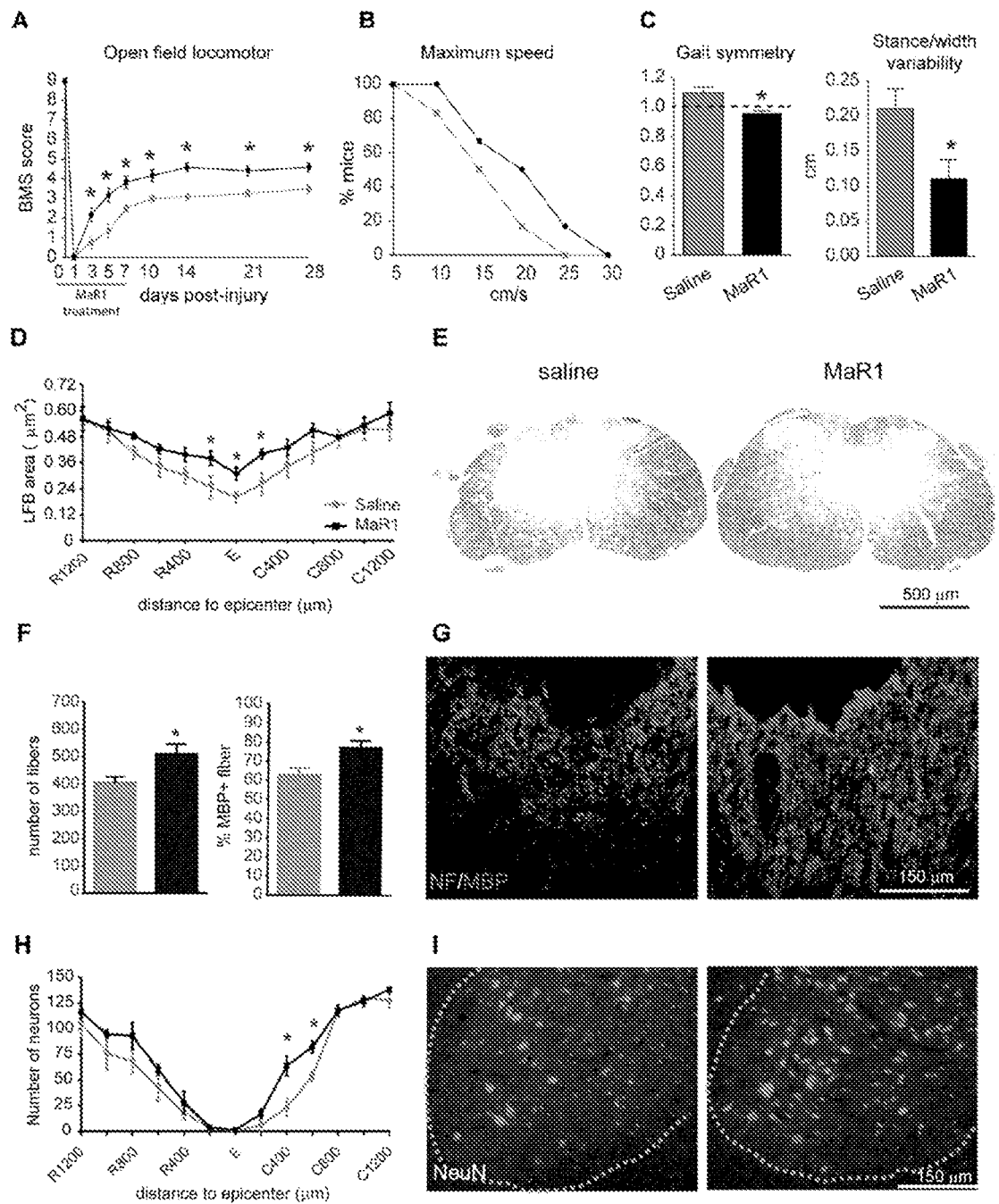
FIG. 8. MaR1 improves locomotor recovery and attenuates secondary tissue damage after SCI. (A) Mice treated with MaR1 show significant improvement in locomotor skills assessed by the 9-point Basso Mouse Scale (BMS) The BMS score of MaR1 treated mice inclined to significantly elevated levels starting at day 3 after injury and remained consistent up the end of the follow up (28 days post-injury) compared with saline treated controls. (B) Mice administered with MaR1 also showed significantly faster speeds of locomotion on the treadmill. (C) DigiGait analysis revealed that MaR1 improved specific parameters of locomotion such as gait symmetry and stance/width stepping variability after SCI, further validating consolidated locomotor control in mice treated with MaR1. (D) Quantification of myelin content at various distances rostral and caudal to the injury epicenter. (E) Representative micrographs showing myelin area at the injury epicenter in section stained with LFB from saline (left image)- and MaR1-treated mice (right image). (F) Quantification of axons (NF+) and myelinated axons (NF+/MBP+) in the dorsal column at the injury epicenter from saline (left image)- and MaR1-treated mice (right image). (G) Representative micrographs showing dorsal neurofilament (red-darker dots) and MBP (green-lighter dots) staining at the injury epicenter from saline (left image)- and MaR1-treated mice (right image). (H) Quantification of ventral horn neuron survival at various distances rostral and caudal to the injury epicenter reveals improved neuronal survival caudal to the lesion in the MaR1 treated group. (I) Representative micrographs showing sparing of ventral horn neurons in saline (left image)- and MaR1-treated mice (right image) tissue in sections stained against NeuN at 400 μm caudal to the injury epicenter. (*$p<0.05$; two-ways RM-ANOVA, Bonferroni's post hoc test in A, D and H; t-test in C and F; (Mantel-Cox test in B; n=10 per group). Data are expressed as mean±SEM.

Administration of MaR1 Reduces Tissue Damage and Improves Locomotor Recovery after SCI We finally examined whether MaR1 improves functional and histological outcomes after SCI. Mice treated with MaR1 demonstrated significant improvement in locomotor recovery resulting in elevated BMS scores. Post hoc analysis revealed significant differences in BMS score starting at day 3 after injury and remaining significantly enhanced up the end of the follow up (FIG. 8A). At 28 dpi, 50% of mice treated with saline showed plantar placement with no stepping, whereas the remaining 50% performed occasional stepping (BMS score of 3.5±0.22). However, all the mice treated with MaR1 displayed plantar placement with occasional or frequent stepping (score 4.58±0.22). Mice administered Marl also showed significantly faster speeds of locomotion on the treadmill (FIG. 8B). In addition, DigiGait analysis revealed that MaR1 improved specific parameters of locomotion such as gait symmetry and stance/width stepping variability after SCI (FIG. 8C), further demonstrating improvement in locomotor control in mice treated with MaR1. No differences were found in other DigiGait parameters.

We then assessed whether the improvement in locomotor function of MaR1-treated mice was associated to reduction of secondary tissue damage after SCI. Histological sections stained with LFB revealed that MaR1 increased myelin content at the injury epicenter and in sections located at 200 µm rostral and caudal to the injury (FIG. 8D, E). To determine whether this greater amount of myelin was due to reduced demyelination or reduced axonal damage or both, we quantified the number of axons (NF+) and those that had myelin sheath (NF/MBP+) in the dorsal columns at the injury epicenter, the most damaged area of the spinal cord. These analyses reveal that MaR1 enhanced both axonal sparing and reduced demyelination after SCI (FIG. 8F, G). In addition, we also found that MaR1 improved neuronal survival in the ventral horn in caudal regions to the injury epicenter (FIG. 8H, I). Overall, these data demonstrate that treatment with MaR1 reduces secondary tissue damage and improves functional outcomes after SCI.

DISCUSSION

Traditionally, therapeutic approaches for acute SCI have sought to modulate the pro-inflammatory limb of the inflammatory response with limited success. Here we identify impaired resolution of inflammation as a prominent feature of the dysregulated inflammatory response after SCI due to incomplete clearance of immune cells from the lesion site. We show that this impaired resolution coincides with severely blunted SPM biosynthesis, in contrast with peripheral, self-resolving inflammatory lesions, which are characterized by an early lipid mediator class shift. Our data reveals that systemic administration of the resolution agonist, namely MaR1, stimulated various biological mechanisms that resulted in improved resolution of inflammation and marked improvement of locomotor outcomes.

Polyunsaturated fatty acids are key regulators of the inflammatory response, since they control several processes involved in the onset and resolution of this physiological process (David et al., 2012c; Serhan, 2014; Serhan et al., 2015). Among them, n-3 PUFA (omega 3-fatty acids) has been specially brought to the attention of the scientific community due to its therapeutic effects in several inflammatory diseases. In particular, the n-3 PUFAs, DHA and EPA, which are enriched in oils derived from fish and algae, are used extensively as dietary supplements, and found to exert beneficial actions in a number of conditions in which the inflammation contributes to the course of pathology, including in SCI (King et al., 2006; Huang et al., 2007; Lopez-Vales et al., 2010).

More recently, EPA and DHA lipid-derived mediators known collectively as SPM, have been identified as key players in the resolution of inflammation and regulators of homeostasis (Schwab et al., 2007; Buckley et al., 2014; Serhan, 2014; Serhan et al., 2015). The importance of SPM in regulating inflammation is evident in many inflammatory disorders such as atherosclerosis, asthma, ulcerative colitis, among others, in which there is absence, or insufficient or delayed production of SPM (Serhan, 2014; Serhan et al., 2015). Importantly, the exogenous administration of SPM reduces inflammation and prevents the detrimental effects exerted by the immune cells, relating the failure in the production of SPM in the pathogenesis of different inflammatory diseases (Serhan, 2014; Serhan et al., 2015). Our results suggest that a similar scenario occurs also after SCI, since the dysregulation of the resolution of inflammation coincides with the inefficient synthesis of SPM.

Among the different family members of SPM, maresins have been the less characterized. This family of SPM derived from macrophages consists of two members, MaR1 (Serhan et al., 2009) and the more recently identified MaR2 (Deng et al., 2014). MaR1 exerts potent actions in regulating inflammation resolution, but also in preventing nociception after inflammatory- and chemotherapy-induced neuropathic pain, and stimulating tissue regeneration in planaria (Serhan et al., 2012; Serhan, 2014). It should be noted that the resolving actions of MaR1 seem to be more potent than those exerted by other resolving agonist, such as RvD1, since it was shown to stimulate greater efferocytosis by human macrophages at 1 nM concentration (Serhan et al., 2012).

Here, we report that daily systemic treatment with very low doses of MaR1 (1 µg/mouse) after SCI accelerates and enhances neutrophil clearance and reduces macrophages accumulation in the lesioned spinal cord, two critical steps for the resolution of inflammation. Since this is, to the best of our knowledge, the first report assessing the effects of MaR1 in the CNS, we investigated the mechanisms underlying the resolving effects of MaR1 in SCI. Recruitment of leukocytes into the lesioned spinal cord is regulated by pro-inflammatory mediators, such as cytokines (David et al., 2012a; Popovich, 2014). MaR1 downregulated expression of cytokines in vitro, also in mouse models of both colitis and acute respiratory distress syndrome (Serhan et al., 2009; Marcon et al., 2013; Abdulnour et al., 2014). Our results in SCI indicate that MaR1 leds to reduced protein levels of several prominent pro-inflammatory cytokines in the spinal cord at 24 h post-injury, including IL-6, CSF3 and different members of chemokine family. Note also that MaR1 did not attenuate the expression of the anti-inflammatory cytokine IL10, suggesting a preferential action of this SPM in reducing pro-inflammatory cytokines.

Cytokines mediate inflammation by acting on specific receptors that activate different intracellular inflammatory cascades. Little is known about the intracellular cascades modulated by MaR1, however, a previous report showed this resolving agent limited NF-kB activation (Marcon et al., 2013). Our results reveal that MaR1 did not abrogate this transcription factor after SCI. Similarly, PI3K/Akt signaling pathway was not affected by this SPM. MaR1 significantly turned off several MAPK and JAK/STAT signaling pathways that are known to exert important pro-inflammatory actions in SCI, without affecting the activation of STAT6, which is required for the suppressive effects of anti-inflammatory cytokines (David et al., 2012b). Both, the cytokine and inflammatory signaling changes after MaR1 at 24 hours post-injury is likely to limit the subsequent infiltration of neutrophils and macrophages in the lesion site, and consequently, accelerate the reduction in their numbers after SCI.

Cytokines and signaling pathways also regulate the phenotype of macrophages. These cells can differentiate into two major types in vitro: (i) M1 macrophages, which display a pro-inflammatory profile and may mediate cytotoxic actions; and (ii) M2 macrophages, which have anti-inflammatory effects and promote tissue healing and repair (Murray et al., 2014; David et al., 2015). However, microglia and macrophages in SCI, cannot be defined within the simple M1-M2 dichotomy described in cell culture conditions, but into a broad spectrum of activation states (David et al., 2015; Francos-Quijorna et al., 2016). MaR1 was previously reported to shift macrophage phenotype towards M2 in cell culture (Dalli et al., 2013). Here, we observed that after SCI, MaR1 did not significantly induced the expression of the classical M2 markers in macrophages, but led to significant reduction in the expression of M1 markers such as iNOS and Ly6C in macrophages, but not microglia. These results therefore suggest that MaR1 skews macrophage activation towards a phenotype more conducive for tissue repair in the lesioned CNS in vivo. Interestingly, this is not the only effect that MaR1 exerted on this leukocyte subset. We also found that the administration of this SPM stimulated macrophages to increase neutrophil phagocytosis in the lesion spinal cord. Earlier studies have shown that MaR1 induced uptake of apoptotic neutrophils and $A\beta_{42}$ in macrophages and microglia, respectively, in culture (Serhan et al., 2012; Zhu et al., 2016). However, this is the first study revealing that, similar to RvD and RvE, MaR1 also promotes neutrophil phagocytosis by macrophages in vivo (Schwab et al., 2007; Serhan, 2014). Therefore, the accelerated and increased clearance of neutrophils observed after SCI by MaR1 treatment could be explained by both, the effects of this immunoresolvent agent on the phagocytic activity of macrophages to clear neutrophils (efferocytosis) and by its suppressive actions on cytokines levels and inflammatory signaling pathway activation. Altogether, we provide clear evidence that MaR1 is effective in enhancing multiple stages of the resolution of inflammation after SCI. These includes, downregulation of cytokines, silencing of inflammatory pathways, reduction of neutrophil and macrophages counts, shift in macrophage phenotype, and stimulation of the phagocytic activity of macrophages. Importantly, all the biological effects induced by MaR1 treatment led to significant improvement in locomotor function and protection against secondary tissue damage. The present results support the concept that the inappropriate biosynthesis of SPM after SCI hampers resolution of inflammation and contributes to the physiopathology of SCI. Since aberrant production of SPM is also reported in the CSF of patients with Alzheimer's disease and multiple sclerosis (Pruss et al., 2013; Zhu et al., 2016) the administration of immunoresolvents may constitute an effective therapeutic avenue for treatment of acute SCI and other neurological conditions in which inflammation contributes to the course of the disease and impaired function.

In the specification and in the claims, the terms "including" and "comprising" are open-ended terms and should be interpreted to mean "including, but not limited to . . . ". These terms encompass the more restrictive terms "consisting essentially of" and "consisting of". It must be noted that as used herein and in the appended claims, the singular forms "a", "an", and "the" include plural reference unless the context clearly dictates otherwise.

LIST OF REFERENCES

Abdulnour R E, Dalli J, Colby J K, Krishnamoorthy N, Timmons J Y, Tan S H, Colas R A, Petasis N A, Serhan C N, Levy B D (2014) Maresin 1 biosynthesis during platelet-neutrophil interactions is organ-protective. Proceedings of the National Academy of Sciences of the United States of America 111:16526-16531.

Arnold L, Henry A, Poron F, Baba-Amer Y, van Rooijen N, Plonquet A, Gherardi R K, Chazaud B (2007) Inflammatory monocytes recruited after skeletal muscle injury switch into antiinflammatory macrophages to support myogenesis. The Journal of experimental medicine 204: 1057-1069.

Basso D M, Fisher L C, Anderson A J, Jakeman L B, McTigue D M, Popovich P G (2006) Basso Mouse Scale for locomotion detects differences in recovery after spinal cord injury in five common mouse strains. J Neurotrauma 23:635-659.

Buckley C D, Gilroy D W, Serhan C N (2014) Proresolving lipid mediators and mechanisms in the resolution of acute inflammation. Immunity 40:315-327.

Coll-Miro M, Francos-Quijorna I, Santos-Nogueira E, Torres-Espin A, Bufler P, Dinarello C A, Lopez-Vales R (2016) Beneficial effects of IL-37 after spinal cord injury in mice. Proceedings of the National Academy of Sciences of the United States of America 113:1411-1416.

Dalli J, Zhu M, Vlasenko N A, Deng B, Haeggstrom J Z, Petasis N A, Serhan C N (2013) The novel 13S,14S-epoxy-maresin is converted by human macrophages to maresin 1 (MaR1), inhibits leukotriene A4 hydrolase (LTA4H), and shifts macrophage phenotype. FASEB journal: official publication of the Federation of American Societies for Experimental Biology 27:2573-2583.

David S, Kroner A (2011) Repertoire of microglial and macrophage responses after spinal cord injury. Nat Rev Neurosci 12:388-399.

David S, Lopez-Vales R, Wee Yong V (2012a) Harmful and beneficial effects of inflammation after spinal cord injury: potential therapeutic implications. Handbook of clinical neurology 109:485-502.

David S, Zarruk J G, Ghasemlou N (2012b) Inflammatory pathways in spinal cord injury. International review of neurobiology 106:127-152.

David S, Greenhalgh A D, Lopez-Vales R (2012c) Role of phospholipase A2s and lipid mediators in secondary damage after spinal cord injury. Cell and tissue research 349:249-267.

David S, Greenhalgh A D, Kroner A (2015) Macrophage and microglial plasticity in the injured spinal cord. Neuroscience 307:311-318.

Deng B, Wang C W, Arnardottir H H, Li Y, Cheng C Y, Dalli J, Serhan C N (2014) Maresin biosynthesis and identification of maresin 2, a new anti-inflammatory and proresolving mediator from human macrophages. PloS one 9:e102362.

Fawcett J W, Schwab M E, Montani L, Brazda N, Muller H W (2012) Defeating inhibition of regeneration by scar and myelin components. Handb Clin Neurol 109:503-522.

Francos-Quijorna I, Amo-Aparicio J, Martinez-Muriana A, Lopez-Vales R (2016) IL-4 drives microglia and macrophages toward a phenotype conducive for tissue repair and functional recovery after spinal cord injury. Glia 64:2079-2092.

Gomez-Nicola D, Perry V H (2015) Microglial dynamics and role in the healthy and diseased brain: a paradigm of functional plasticity. Neuroscientist 21:169-184.

Hassan I R, Gronert K (2009) Acute changes in dietary omega-3 and omega-6 polyunsaturated fatty acids have a pronounced impact on survival following ischemic renal injury and formation of renoprotective docosahexaenoic acid-derived protectin D1. Journal of immunology 182:3223-3232.

Hawthorne A L, Popovich P G (2011) Emerging concepts in myeloid cell biology after spinal cord injury. Neurotherapeutics: the journal of the American Society for Experimental NeuroTherapeutics 8:252-261.

Huang W L, King V R, Curran O E, Dyall S C, Ward R E, Lal N, Priestley J V, Michael-Titus A T (2007) A combination of intravenous and dietary docosahexaenoic acid significantly improves outcome after spinal cord injury. Brain 130:3004-3019.

King V R, Huang W L, Dyall S C, Curran O E, Priestley J V, Michael-Titus A T (2006) Omega-3 fatty acids improve recovery, whereas omega-6 fatty acids worsen outcome, after spinal cord injury in the adult rat. The Journal of neuroscience: the official journal of the Society for Neuroscience 26:4672-4680.

Kroner A, Greenhalgh A D, Zarruk J G, Passos Dos Santos R, Gaestel M, David S (2014) TNF and increased intracellular iron alter macrophage polarization to a detrimental M1 phenotype in the injured spinal cord. Neuron 83:1098-1116.

Lopez-Vales R, Redensek A, Skinner T A, Rathore K I, Ghasemlou N, Wojewodka G, DeSanctis J, Radzioch D, David S (2010) Fenretinide promotes functional recovery and tissue protection after spinal cord contusion injury in mice. The Journal of neuroscience: the official journal of the Society for Neuroscience 30:3220-3226.

Lu Y, Belin S, He Z (2014) Signaling regulations of neuronal regenerative ability. Curr Opin Neurobiol 27:135-142.

Marcheselli V L, Hong S, Lukiw W J, Tian X H, Gronert K, Musto A, Hardy M, Gimenez J M, Chiang N, Serhan C N, Bazan N G (2003) Novel docosanoids inhibit brain ischemia-reperfusion-mediated leukocyte infiltration and pro-inflammatory gene expression. The Journal of biological chemistry 278:43807-43817.

Marcon R, Bento A F, Dutra R C, Bicca M A, Leite D F, Calixto J B (2013) Maresin 1, a proresolving lipid mediator derived from omega-3 polyunsaturated fatty acids, exerts protective actions in murine models of colitis. Journal of immunology 191:4288-4298.

Murray P J et al. (2014) Macrophage activation and polarization: nomenclature and experimental guidelines. Immunity 41:14-20.

Nahrendorf M, Swirski F K, Aikawa E, Stangenberg L, Wurdinger T, Figueiredo J L, Libby P, Weissleder R, Pittet M J (2007) The healing myocardium sequentially mobilizes two monocyte subsets with divergent and complementary functions. The Journal of experimental medicine 204:3037-3047.

Popovich P G (2014) Neuroimmunology of traumatic spinal cord injury: a brief history and overview. Experimental neurology 258:1-4.

Popovich P G, Longbrake E E (2008) Can the immune system be harnessed to repair the CNS? Nat Rev Neurosci 9:481-493.

Pruss H, Kopp M A, Brommer B, Gatzemeier N, Laginha I, Dirnagl U, Schwab J M (2011) Non-resolving aspects of acute inflammation after spinal cord injury (SCI): indices and resolution plateau. Brain Pathol 21:652-660.

Pruss H, Rosche B, Sullivan A B, Brommer B, Wengert O, Gronert K, Schwab J M (2013) Proresolution lipid mediators in multiple sclerosis—differential, disease severity-dependent synthesis—a clinical pilot trial. PloS one 8:e55859.

Santos-Nogueira E, Lopez-Serrano C, Hernandez J, Lago N, Astudillo A M, Balsinde J, Estivill-Torrus G, de Fonseca F R, Chun J, Lopez-Vales R (2015) Activation of Lysophosphatidic Acid Receptor Type 1 Contributes to Pathophysiology of Spinal Cord Injury. The Journal of neuroscience: the official journal of the Society for Neuroscience 35:10224-10235.

Schwab J M, Chiang N, Arita M, Serhan C N (2007) Resolvin E1 and protectin D1 activate inflammation-resolution programmes. Nature 447:869-874.

Serhan C N (2014) Pro-resolving lipid mediators are leads for resolution physiology. Nature 510:92-101.

Serhan C N, Dalli J, Colas R A, Winkler J W, Chiang N (2015) Protectins and maresins: New pro-resolving families of mediators in acute inflammation and resolution bioactive metabolome. Biochim Biophys Acta 1851:397-413.

Serhan C N, Yang R, Martinod K, Kasuga K, Pillai P S, Porter T F, Oh S F, Spite M (2009) Maresins: novel macrophage mediators with potent antiinflammatory and proresolving actions. The Journal of experimental medicine 206:15-23.

Serhan C N, Dalli J, Karamnov S, Choi A, Park C K, Xu Z Z, Ji R R, Zhu M, Petasis N A (2012) Macrophage proresolving mediator maresin 1 stimulates tissue regeneration and controls pain. FASEB journal: official publication of the Federation of American Societies for Experimental Biology 26:1755-1765.

Steinman L (2015) No quiet surrender: molecular guardians in multiple sclerosis brain. J Clin Invest 125:1371-1378.

Stenudd M, Sabelstrom H, Frisen J (2015) Role of endogenous neural stem cells in spinal cord injury and repair. JAMA Neurol 72:235-237.

Svensson C I, Zattoni M, Serhan C N (2007) Lipoxins and aspirin-triggered lipoxin inhibit inflammatory pain processing. The Journal of experimental medicine 204:245-252.

Zhu M, Wang X, Hjorth E, Colas R A, Schroeder L, Granholm A C, Serhan C N, Schultzberg M (2016) Pro-Resolving Lipid Mediators Improve Neuronal Survival and Increase Abeta42 Phagocytosis. Molecular neurobiology 53:2733-2749.

The invention claimed is:

1. A method for treating a central nervous system (CNS) injury comprising administering a therapeutically effective amount of a composition comprising isolated maresin-1 to a subject in need thereof, wherein the CNS injury is spinal cord injury or, traumatic brain injury, and wherein the administration of the composition comprising isolated maresin-1 results in:
   (i) increased myelin content at the injury epicenter,
   (ii) improved neuronal survival at the injury epicenter,
   (iii) improved locomotor recovery,
   (iv) reduced demyelination at the injury epicenter,
   (v) reduced axonal damage at the injury epicenter, or
   (vi) a combination thereof.

2. The method of claim 1, wherein the composition comprising isolated maresin-1 is further combined with at least one specialized pro-resolving lipid mediator selected from the group consisting of other maresin, resolvin D1, resolvin D2, resolvin D3, resolvin D4, resolvin E1, resolvin E2, protectin D1, neuroprotection D1, lipoxin A4, and aspirin-triggered lipoxin.

3. The method of claim 1, wherein the composition comprising isolated maresin-1 is formulated as a pharmaceutical composition, food, functional food, food ingredient or supplement, nutritional supplement, nutraceutical composition or medical food or is in the extract of a natural product or cosmetic composition.

4. The method of claim 3, wherein the composition comprising isolated maresin-1 is a pharmaceutical composition.

5. The method of claim 3, wherein the composition comprising isolated maresin-1 is a food, functional food, or a food ingredient or supplement.

6. The method of claim 3, wherein the composition comprising isolated maresin-1 is a nutraceutical composition or a medical food.

7. The method of claim 3, wherein the composition comprising isolated maresin-1 is a cosmetic composition.

8. The method of claim 1, wherein the composition comprising isolated maresin-1 is administered by oral, intravenous, subcutaneous, intramuscular, rectal, topical, vaginal, parenteral, transdermal, intraperitoneal, intrapulmonary, intrathecal or intranasal route.

9. The method of claim 8, wherein the composition comprising isolated maresin-1 is administered by oral or parenteral route.

10. The method of claim 1, wherein the administration of the composition comprising isolated maresin-1 results in a reduction in inflammation.

11. The method of claim 1, wherein the administration of the composition comprising isolated maresin-1 results in
   (i) enhanced neutrophil clearance,
   (ii) resolution of neutrophil inflammation,
   (iii) late macrophages clearance,
   (iv) reduced macrophage accumulation,
   (v) reduced chemokine expression,
   (vi) attenuation of secondary tissue damage, or
   (vii) any combination thereof.

12. The method of claim 1, wherein the subject is a human subject.

13. The method of claim 11, wherein the chemokine is a pro-inflammatory cytokine.

14. The method of claim 13, wherein the pro-inflammatory cytokine is an interleukin.

15. The method of claim 14, wherein the interleukin is selected from the group consisting of IL-3, IL-6, IL-13, and combinations thereof.

16. The method of claim 13, wherein the pro-inflammatory cytokine is selected from the group consisting of IL-3, IL-5, IL-13, CSF3, CXCL1, CXCL2, CXCL5, CCL3, CCL4, and combinations thereof.

17. The method of claim 1, wherein the composition comprising isolated maresin-1 is administered daily.

* * * * *